United States Patent

Leigh et al.

[11] Patent Number: 5,670,506
[45] Date of Patent: Sep. 23, 1997

[54] HALOGEN, ISOTHIOCYANATE OR AZIDE SUBSTITUTED XANTHINES

[75] Inventors: Alistair Leigh, Brier; John Michnick; Anil Kumar, both of Seattle; Gail Underiner, Brier, all of Wash.

[73] Assignee: Cell Therapeutics, Inc., Seattle, Wash.

[21] Appl. No.: 42,946

[22] Filed: Apr. 5, 1993

[51] Int. Cl.$^6$ .................... A61K 31/52; C07D 473/00
[52] U.S. Cl. .................... 514/258; 514/263; 544/267; 544/272; 544/277
[58] Field of Search .................... 544/267, 276, 544/272, 277; 514/258

[56] References Cited

U.S. PATENT DOCUMENTS

| | | | |
|---|---|---|---|
| 4,289,776 | 9/1981 | Mohler et al. | 424/253 |
| 4,766,142 | 8/1988 | Arcamone et al. | 514/422 |
| 4,942,166 | 7/1990 | Harnden et al. | 544/276 |
| 4,952,679 | 8/1990 | Hoegerle et al. | 534/618 |
| 5,086,056 | 2/1992 | Janssens et al. | 514/253 |
| 5,126,349 | 6/1992 | Deford et al. | 514/269 |
| 5,250,535 | 10/1993 | Verheyden et al. | 544/276 |
| 5,298,508 | 3/1994 | Jacobson et al. | 514/263 |

FOREIGN PATENT DOCUMENTS

| | | | |
|---|---|---|---|
| 461196 | 10/1977 | Japan | 544/267 |
| 2122197 | 1/1984 | United Kingdom | 544/276 |

OTHER PUBLICATIONS

Kanehira et al. Chem. Abst. 110:212848x, p. 757; 1989.

*Primary Examiner*—Mukund J. Shah
*Assistant Examiner*—Pavanaram K. Sripada
*Attorney, Agent, or Firm*—Stephen Faciszewski

[57] ABSTRACT

There is disclosed a compound having the formula:

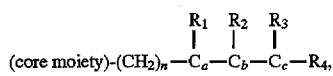

wherein n is an integer from 5 to 9, wherein the core moiety is a heterocylic moiety wherein $C_a$, $C_b$, and $C_c$ are an R or S enantiomer or racemic mixture and the $C_a$, $C_b$, and $C_c$ carbon atoms are bonded together by a single bond, double bond, ether or ester linkages, wherein $R_1$, $R_2$ and $R_3$ are independently halo, hydroxy, hydrogen, keto, isothiocyano, azide or haloacetoxy with the proviso that at least one of $R_1$, $R_2$ or $R_3$ must be a halo, isothiocyano, azide or haloacetoxy group, wherein $R_4$ is hydrogen, $C_{1-6}$ alkyl, $C_{1-6}$ alkenyl, cyclo $C_{4-6}$ alkyl, or phenyl, and wherein halo refers to fluoro, chloro, bromo and iodo and salts thereof and pharmaceutical compositions thereof.

17 Claims, 14 Drawing Sheets

HALOGEN, ISOTHIOCYANATE OR AZIDE SUBSTITUTED XANTHINES

TECHNICAL FIELD OF THE INVENTION

The invention relates to a class of halogen substituted heterocyclic compounds that are effective agents to modulate cellular responses to noxious or inflammatory stimuli, or to directly be antimicrobial to yeast or fungal infections. More specifically, the inventive compounds have at least one halogen group bonded to a hydrocarbon substituent bonded to a ring nitrogen of a heterocyclic core. The inventive compounds are useful anatagonists to control intracellular levels of specific sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,107 and 3,737,433. Metabolites of PTX were summarized in Davis et al., *Applied Environment Microbiol.* 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947. In addition, U.S. Pat. Nos. 4,833,146 and 5,039,666 disclose use of tertiary alcohol analogs of xanthine for enhancing cerebral blood flow.

Furthermore, U.S. Pat. No. 4,636,507 describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective therapeutic compounds that are safe and effective for human or animal administration and that can maintain cellular homeostasis in the face of a variety of inflammatory stimuli. The present invention was made in a process of looking for such compounds.

SUMMARY OF THE INVENTION

We have found that the compounds described herein can be used to maintain homeostasis of a large variety of target cells in response to a variety of stimuli. In addition, the inventive compounds and compositions are suitable for normal routes of therapeutic administration and permit effective dosages to be provided.

The invention is directed to the use of a class of halogen, isothiocyanate, or azide substituted compounds, salts or free bases thereof. The inventive compounds are effective in modulating cellular response to external or in situ primary stimuli, as well as to specific modes of administration of such compounds in effective amounts.

The present invention provides compounds and pharmaceutical compositions comprising a compound having the formula:

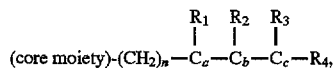

wherein n is an integer from 5 to 9, wherein the core moiety comprises at least one five to seven-membered ring or an open chain analog of such a ring group, wherein $C_a$, $C_b$, and $C_c$ are an R or S enantiomer or racemic mixture and the $C_a$, $C_b$, and $C_c$ carbon atoms are bonded together by a single bond, double bond, ether or ester linkages, wherein $R_1$, $R_2$ and $R_3$ are independently halo, hydroxy, hydrogen, keto, isothiocyano, azide or haloacetoxy with the proviso that at least one of $R_1$, $R_2$ or $R_3$ must be a halo, isothiocyano, azide or haloacetoxy group, wherein $R_4$ is hydrogen, $C_{1-6}$ alkyl, $C_{1-6}$ alkenyl, cyclo $C_{4-6}$ alkyl, or phenyl, and wherein halo refers to fluoro, chloro, bromo and iodo.

Preferably, one of $R_1$, $R_2$ and $R_3$ is a hydrogen (most preferably $R_2$), and $R_1$ and $R_3$ are independently a halo (most preferably a chloro or fluoro) and a keto or a hydroxy group, and n is preferably an integer from 5–6. Most preferably, the compound is R and S enantiomers and racemic mixtures of compounds selected from the group consisting of 1-(5-isothiocyanatohexyl)3,7-dimethylxanthine (CT2519), 1-(6-chloro-5-oxohexyl)3,7-dimethylxanthine (CT1595), 1-(6-azidohexyl)3,7-dimethylxanthine (CT2557), 1-(9-acetoxy-10-bromodecyl) 3,7-dimethylxanthine (CT1583), 1-(5-fluorohexyl)3,7-dimethylxanthine (CT1577), 1-[5-(chloroacetoxy)hexyl]3,7-dimethylxanthine (CT1529), 1-[6-(chloroacetoxy)hexyl]3,7-dimethylxanthine (CT1527), 1-(6-chlorohexyl)3,7-dimethylxanthine (CT1525), 1-(6-azido-5-hydroxyhexyl)3,7-dimethylxanthine (CT1517), 1-(7-acetoxy-8-bromooctyl) 3,7-dimethylxanthine (CT1514), 1-(5-acetoxy-6-bromohexyl)-3-methylbenzoyleneurea (CT1205), 3-(8-acetoxy-9-bromononyl)-1-methyluracil (CT1801), and 3-(8-acetoxy-9-bromononyl)-1-methylthymine (CT1908).

Preferably, the core moiety has from one to three, five to six membered ring structures in a predominantly planar structure. Preferably, the halo, isothiocyanate or azide substituent is bonded to a ring nitrogen on the core moiety if one exists.

For example, the core moiety is selected from the group consisting of xanthine, halogen-substituted xanthines, 3,7-dimethylxanthine, 3-methylxanthine, 3-methyl-7-methylpivaloylxanthine, 8-amino-3-methylxanthine, 7-methylhypoxanthine, 1-methyluracil, 1-methylthymine, 1-methyl-5,6-dihydrouracil, glutarimides, phthalimide, 1-methyl-2,4(1H,3H)-quinazolinedione (1-methylbenzoyleneurea), 6-aminouracil, homophthalimide, succinimide, 1,3-cyclohexanedione, resorcinol, 1,3-dihydroxynaphthalene, 1,3-cyclopentanedione, 1,3-dimethyldihydroxypyrazolo[4,3-d]pyrimidine, 5-substituted uracils, 6-substituted uracils, 1-methylpyrrolo [2,3-d]pyrimidine, 1-methyllumazine, imidazole amides, 2-pyrrole amides, 3-pyrrole amides, benzamides, methylbarbituric acid, benzene, piperdine, delta-lactam, 2-hydroxypyridine, 1,2,3,4-tetrahydroisoquinolone, isocarbostyril, and quinazolin-4 (3H)-one. Most preferably, the heterocyclic core is a xanthine. The core moiety can also include a non-cyclic group. Examples of non-cyclic core groups include open chain analogs of glutarimide, carboxylic acid, a hydroxyl group, sulfone, sulfonate, and the like.

The present invention further provides a pharmaceutical composition comprising an inventive compound and a pharmaceutically acceptable excipient, wherein the pharmaceutical composition is formulated for oral, parenteral or topical administration to a patient.

The present invention further provides a method for treating an individual having a variety of diseases, wherein the disease is characterized by or can be treated by inhibiting an immune response or a cellular response to external or in situ primary stimuli, wherein the cellular response is mediated through a specific phospholipid-based second messenger acting adjacent to the inner leaflet of the cell membrane of a cell. The second messenger pathway is activated in response to various noxious or proliferative stimuli characteristic of a variety of disease states and the biochemistry of this second messenger pathway is described herein. More specifically, the invention is directed to methods to treat or prevent clinical symptoms of various disease states or reduce toxicity's of other treatments by inhibiting cellular signaling through the second messenger pathway described herein. The disease states or treatment-induced toxicity's are selected from the group consisting of proliferation of tumor cells in response to an activated oncogene; hematocytopenia caused by cytoreductive therapies; autoimmune diseases caused by a T cell response, monocyte response or a B cell response and antibody production; acute inflammatory disease such as septic shock or hemmorosic shock; resistance of mesenchymal cells to tumor necrosis factor (TNF); chronic inflammatory disease characterized by T cell, glial, astrocyte or monocyte adhesion, migration and/or release of inflammatory stimuli and metalloproteases, such as rheumatoid arthritis, osteoarthritis, multiple sclerosis or insulin dependent diabetes mellitus (IDDM); proliferation of smooth muscle cells endothelial cells, fibroblasts and other cell types in response to growth factors, such as PDGF-AA, BB, FGF, EGF, etc. (i.e., atherosclerosis, restenosis, stroke, and coronary artery disease); human immunodeficiency virus infection (AIDS and AIDS related complex); proliferation of kidney mesangial cells in response to IL-1 Mip-1α, PDGF or FGF; inflammation; kidney glomerular or tubular toxicity in response to cyclosporin A or amphotericin B treatment; organ toxicity (e.g., gastrointestinal or pulmonary epithelial) in response to a cytoreductive therapy (e.g., cytotoxic drug or radiation); enhancing antitumor effects of nonalkylating antitumor agents; inflammation in response to inflammatory stimuli (e.g., TNF, IL-1 and the like) characterized by production of metalloproteases or allergies due to degranulation of mast cells and basophils in response to IgE or RANTES, bone diseases caused by overproduction of osteoclast-activating factor (OAF) by osteoclasts, CNS diseases caused by reduced signal transduction of the neurotransmitters epinephrine and acetylcholine, and combinations thereof. The inventive compounds are also useful as antimicrobial agents to directly treat fungal or yeast infections and to indirectly treat bacterial or viral infections through an immune stimulation and pro-hematopoietic effect.

BRIEF DESCRIPTION OF THE DRAWINGS

As shown in FIG. 6, CT1595 inhibited strongly inhibited yeast growth and is a potential topical or systemic antimicrobial drug according to this in vitro model.

FIG. 7 shows that all drugs were active in this predictive in vitro model. However CT1595 and CT2519 were the most potent compounds with IC50 values below 10 μM.

DETAILED DESCRIPTION OF THE INVENTION

Figure 1:
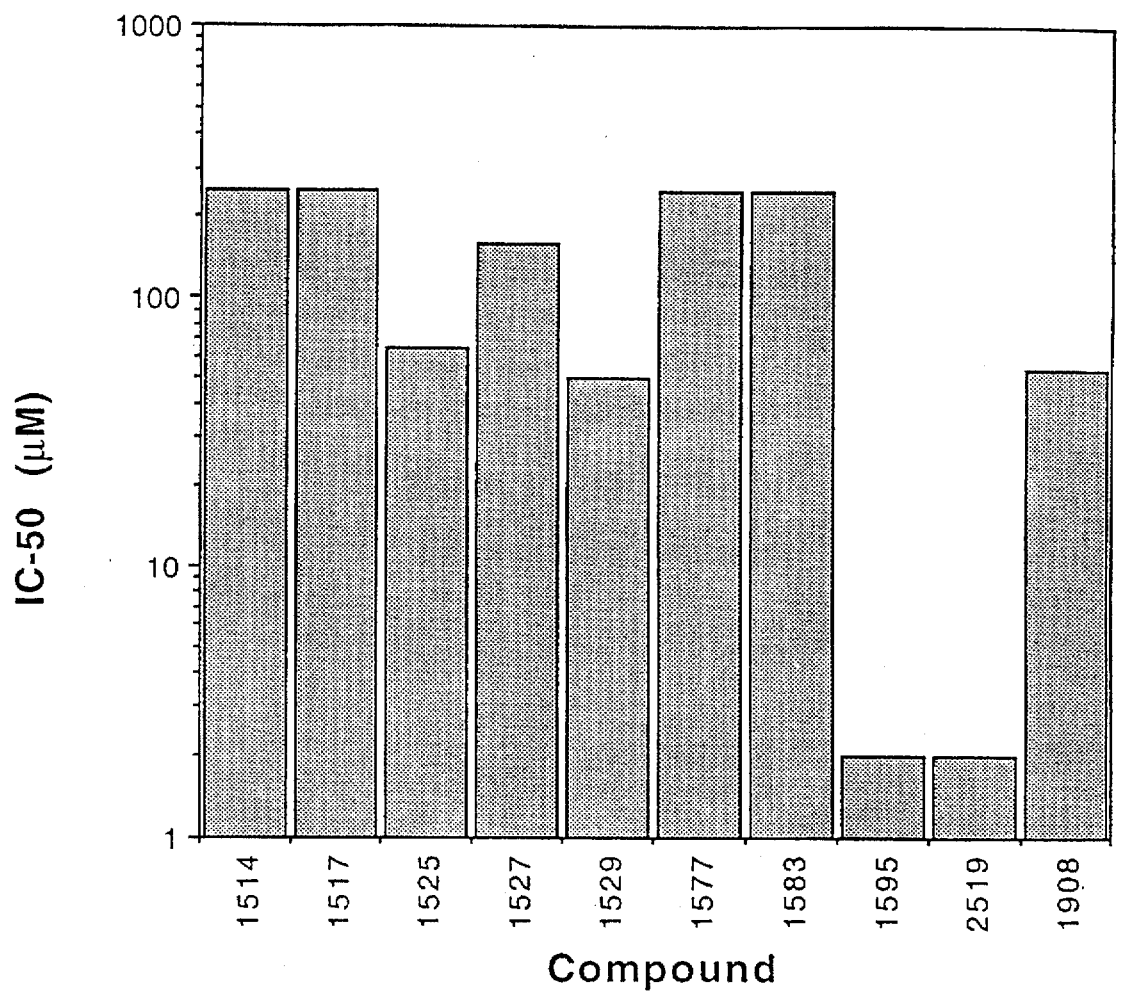
FIG. 1 shows a bar graph of IC50 values for five inventive compounds (see Table 1 below for chemical names) in a mixed lymphocyte assay to measure immune suppression activity. CT1930 did not exhibit meaningful immune suppression activity, but CT2523 was the most potent compound. The mixed lymphocyte reaction shows a proliferative response of PBMC (peripheral blood mononuclear cells) to allogeneic stimulation determined in a two-way mixed lymphocyte reaction. CT1595 and CT2519 showed dose-response activity in this immune modulating activity assay procedure with an IC50's below of 10 μM, at levels easily achievable in vivo.

The invention is directed to a defined genus of inventive compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline
"remodeled" PA, cyclic pathway=PAA, LPA, PA and DAG intermediates substituted with 1-saturated, 2linoleoyl or 1,2-dioleoyl, dioleoy/1,2-sn-dilinoleoyl at the indicated sn-1 and sn-2 positions.
"Classical PI Pathway"=PI, DAG, PA intermediates substituted with 1-stearoyl, 2-arachidonoyl fatty acyl side chains.
"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl, 2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. However, it is important to know whether or not each phospholipid species passes through a PA form previous to hydrolysis to DAG. The lyso-PA that is converted to PA and thence to DAG may be shown. The complexities of this second messenger pathway can be sorted by suitable analyses by fatty acyl side chain chemistry (i.e., by thin layer chromatography, gas-liquid chromatography, or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through the action of PAPH. Several minutes later, DAG is generated from PI through the classical phosphoinositide pathway. In many cells, DAG is derived from both PA that is being remodeled through a cycle whereby PA is sn-2 hydrolyzed by PLA-2, followed by sn-2 transacylation by LPAAT, and a PLD-pathway from PA that is generated from either PE or PC or both substrates by PLD.

A method described here permits differentiation of the various subspecies of PA and DAG based upon acyl chain composition. This can differentiate those compounds that activate (and inhibit activation of) the present second messenger pathway from other pathways, such as the classical PI pathway. The present second messenger pathway involves substrates with unsaturated fatty acids in the sn-2 position other than arachidonate and those sub species of PAPH and LPAAT that are not involved in normal cellular housekeeping functions that are part of the classical PI pathway. The PAPH and LPAAT enzymes involved in the present second messenger pathway are exquisitely stereo specific for different acyl side chains and isomeric forms of substrates.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g., 1,2-sn-dioleoyl DAG, 1-alkyl,2-linoleoyl DAG and 1-alkyl,2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

Therapeutic Uses of the Inventive Compounds

The compounds of the invention provide a mechanism to maintain homeostasis in cells contacted by primary stimuli through mitigating the effects of these primary stimuli on the secondary signaling pathways invoked within seconds of the primary stimulus. For example, administration of the inventive compounds in vivo or ex vivo provide a method to modify cellular behavior which method comprises contacting cells (in vivo or ex vivo) whose behavior is to be modified with an effective amount of an inventive compound or a pharmaceutical composition thereof wherein said method is: (1) a method to inhibit proliferation of tumor cells and said amount is sufficient to inhibit said proliferation; or (2) a method to promote differentiation of hematopoietic stem cells into red blood cells, platelets, lymphocytes, and granulocytes, and said amount is sufficient to promote said proliferation; or (3) a method to suppress activation of T-cells by antigen or IL-2 stimulation, and said amount is sufficient to promote said activation; or (4) a method to suppress activation of monocyte/macrophage cells by endotoxin, TNF, IL-1 or GM-CSF stimulation and said amount is sufficient to suppress said activation; or (5) a method to enhance the resistance of mesenchymal cells to the cytotoxic effect of tumor necrosis factor and said amount is sufficient to enhance said resistance; or (6) a method to suppress antibody production of B-cells in response to an antigen, IL-4 or CD40 ligand and said amount is sufficient to suppress said antibody production; or (7) a method to inhibit the proliferation of smooth muscle cells in response to growth factors capable of stimulating said proliferation and said amount is sufficient to inhibit said proliferation; or (8) a method to lower systemic vascular resistance conferred by endothelial cells and said amount is sufficient to reduce the release of hypertension-inducing substances; or (9) a method to lower systemic vascular resistance induced by endothelial cells and said amount is sufficient to enhance the release of anti-hypertensive substances; or (10) a method to lower expression of adhesion molecules induced by enhancers thereof, and said amount is sufficient to lower said expression; or (11) a method to suppress the activation of T-cells by HIV and said amount is sufficient to suppress said activation thus inhibiting viral replication; or (12) a method to inhibit the proliferation of kidney mesangial cells in response to stimulation by IL-1 and/or mip-1α and/or PDGF and/or FGF and said amount is sufficient to inhibit said proliferation; or (13) a method to enhance the resistance of kidney glomerular or tubular cells to cyclosporin A or amphotericin B and said amount is sufficient to enhance said resistance; or (14) a method to prevent the suppression of growth stimulatory factor production in TNF-treated bone marrow stromal cells and said amount is sufficient to prevent said suppression; or (15) a method to prevent the release of mip-1α by IL-1, TNF, or endotoxin stimulated monocytes and macrophages; or (16) a method to prevent the release of platelet activating factor by IL-1, TNF, or endotoxin treated megakaryocytes, fibroblastic cells, and macrophages; or (17) a method to prevent the down-regulation of receptors for cytokines in TNF-treated hematopoietic progenitor cells and said amount is sufficient to prevent said down-regulation; or (18) a method to suppress the production of metalloproteases in IL-1-stimulated or TNF-stimulated glomerular epithelial cells or synovial cells and said amount is sufficient to enhance said production; or (19) a method to enhance the resistance of gastrointestinal or pulmonary epithelial cells to cytotoxic drugs or radiation and said amount is sufficient to enhance said resistance; or (20) a method to enhance the antitumor effect of a non-alkylating antitumor agent and said amount is sufficient to enhance said effect, or (21) a method to inhibit the production of osteoclast activating factor in response to IL-1, and said amount is sufficient to inhibit said production, or (22) a method to inhibit degranulation in response to IgE, and said amount is sufficient to inhibit said degranulation, or (23) a method to enhance the release of adrenergic neural transmitters, dopamine, norepinephrine, or epinephrine, or the neurotransmitter, acetylcholine, and said amount is sufficient to enhance said release, or (24) a method to modulate the post-synaptic "slow current" effects of the adrenergic neurotransmitters dopamine, epinephrine, or norepinephrine, or the neurotransmitter acetylcholine, and said amount is sufficient to modulate such slow currents.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. Inventive compounds are able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation. In addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, coronary artery disease, atherosclerosis, hypertension, unwanted immune response, viral infection, nephritis, mucositis, and various allergic responses. Prevention of allergic responses include prevention of acute allergic response and thus moderation or prevention of rhinorrhea, sinus drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV 1, changes in vital capacity, and extensive mucus production.

Other suitable subjects for the administration of compounds of the invention, include patients being administered cytoreductive agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strychnine, to potentiate the effect of anti-Parkinson drags such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiting such treatment as an effective oral, parenteral, or intravenous sublethal dose of about 200 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

The specific inhibition of activation of the specific second messenger pathway that is activated primarily by various noxious stimuli, provides the inventive compounds with an ability to be used to treat a wide variety of clinical indications. Moreover, the in vitro and in vivo data presented herein provides predictive data of a wide variety of clinical indications that share a common thread of activation of the specific second messenger pathway, whose activation by noxious stimuli mediated through, for example, inflammatory cytokines, is specifically inhibited by the inventive compounds. In fact, it is this mechanism of action of the inventive compounds that explains why the inventive compounds can have a wide variety of different clinical indications. Activation of the present second messenger pathway is a major mediator of response to noxious stimuli and results in cellular signals that lead to, for example, intimation, immune response, inhibition of blood cell regeneration and cancer cell growth. However, not all inhibitors inhibit all enzymes of this second messenger pathway. The inventive compounds are most effective mediators of inflammation and inhibition of blood cell regeneration. Signals mediated by the present second messenger pathway include, for example, those cellular responses of LPS directly, T cell activation by antigen, B cell activation by antigen, cellular responses to IL-1 mediated through the IL-1 Type 1 receptor (but not the IL-1 Type 2 receptor), the TNF Type 1 receptor, activated oncogenes (e.g., ras, abl, her2-neu and the like), low affinity GM-CSF (granulocyte macrophage colony stimulating factor) receptor, and smooth muscle cell proliferation stimulated by PDGF, b-FGF and IL-1. There are other signals that are not mediated through the present second messenger pathway, and these include proliferation of hematopoietic cells induced by G-CSF (granulocyte colony stimulating factor), interleukin-3 (IL-3), SCF (stem cell factor) and GM-CSF; neutrophil activation induced by interleukin-8 (IL-8) or leukotriene B4; T cell proliferation in response to IL-2; and endothelial cell proliferation in response to acidic FGF (fibroblast growth factor).

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle and kidney mesengial cells; (2) suppresses up regulation of adhesion molecules as shown, for example, by blocking VCAM in endothelial cells of CD18 in neutrophils; (3) inhibiting TNF, LPS and IL-1 induced metalloproteases (an inflammation model); (4) block LPS, TNF or IL-1 induced cellular activation (for prevent and treatment of septic shock or sepsis syndrome); (5) suppress T cell and B cell activation by antigen of by cross-linking CD3 complex; (6) inhibit mast cell activation by IgE; and (7) suppress malignant phenotype in transformed cells and tumor cell lines.

The foregoing in vitro effects give rise to the following in vivo biologic effects, including, but not limited to, protection and treatment of endotoxic shock and sepsis induced by gram positive or gram negative bacteria, inhibition of tumor cell growth, stimulation of hematopoiesis following cytoreductive therapy, synergistic immumosuppression in preventing GVHD (graft versus host disease), and stimulation of hair grow through reversal of an apoptotic process. The inventive compounds are most potent when used to stimulate hematopoiesis, prevent and treat septic shock, treat acute and chronic inflammatory disease, treat or prevent an autoimmune disease, treat a fungal or yeast infection, and stimulate hair growth (when applied topically).

The inventive compounds also are useful as an adjuvant to inhibit toxic side effects of drugs whose side effects are mediated through the present second messenger pathway. These side effects include, for example, side effects of interleukin-2 (IL-2), renal side effects of cyclosporin A and FK506, and side effects of amphotericin B. It should be noted that the inventive compounds inhibit antigen-induced T cell activation, like cyclosporin or FK506, but, unlike cyclosporin or FK506, do not prevent generation of NK and LAK cells, do not suppress IL-2 release from T cells and do not suppress IL-8 release.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. PTX, by contrast in the same experiment, only inhibited PUMP-1 activity to 95% of its control levels which was not significant. Accordingly, the inventive compounds prevent induction of certain metalloproteases induced by IL-1 or TNF and are not involved with constitutively produced proteases (e.g., 72 kD type IV collagenase) involved in normal tissue remodeling.

It appears that some oncogenes signal and are active through the second messenger pathway described herein. Therefore, compounds that can inhibit this pathway, such as the inventive compounds, can be cytotoxic to transformed cells at lower doses than they are cytotoxic to non-transformed cells. This differential toxicity, together with careful dosing, provides a method of using the inventive compounds as cancer chemotherapeutic agents with limited toxicity's for normal tissue. In fact, CT1595 exhibits such activity and therapeutic usefulness in assay described herein.

The inventive compounds inhibit signal transduction mediated through the Type I IL-1 receptor, and are therefore considered as IL-1 antagonists. A review article entitled "The Role of Interleukin-1 in Disease" (Dinarello and Wolff *N. Engl. J. Med.* 328:106, 1993) described the role of IL-1 as "an important rapid and direct determinant of disease." "In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, "the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure, and doses of 300 ng or more per kilogram of body weight may cause severe hypotension." "The therapeutic advantage of blocking the action of IL-1 resides in preventing its deleterious biologic effects without interfering with the production of molecules that have a role in homeostasis." The present inventive compounds address the need identified by Dinarello and Wolff by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$) and leukotriene $B_4$ ($LTB_4$) and IL-8, an inflammatory cytokine with neutrophil-chemoattractant and neutrophil-stimulating properties. Tissue concentrations of PGE2 and LTB4 correlate with the severity of disease in patients with ulcerative colitis, and tissue concentrations of IL-1 and IL-8 are high in patients with inflammatory bowel disease. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans mediated by immunocompetent cells. Islets of animals with spontaneously occurring IDDM (e.g., BB rats or NOD mice) have inflammatory cells that contain IL-1. Therefore, the inventive compounds should be useful for the prevention of and treatment of IDDM.

IL-1 also plays a role in the development of atherosclerosis. Endothelial cells are a target of IL-1. IL-1 stimulates proliferation of vascular smooth muscle cells. Foam cells isolated from fatty arterial plaques from hypercholesterolemic rabbits contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. Activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and 1-o-alkyl or 1-o-alkenyl acylglycerol (AAG) species. The inventive compounds exert their activity by inhibiting one or both enzymes at the inner leaflet of the plasma membrane. Therefore, appropriate in vitro models for drug activity is to measure inhibition of stimulation caused by a pro-inflammatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is about <0.1% of total membrane lipid mass, is sufficient to activate PLD activity. This quantity of PA is similar to that endogeneously synthesized by LPAAT. The PA-stimulated PLD acts upon PE, which should be localized to the inner leaflet of the cell membrane, which is enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 min) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG on stimulation with mitogens, although the sources of DAG have differed between experimental systems. In nontransformed renal mesangial cells, IL-1β stimulation increased PLA2 and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. The specific species of DAG that is stimulated by serum is dioleoyl and for PA are dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an upregulation of PA through indirect stimulation of PLA2 and/or LPAAT activity. The inventive compounds and PTX inhibit the conversion of the upregulated lysoPA to PA and subsequently block the phenotypic changes induced by PA/DAG in the membrane.

The ability of the inventive compounds and PTX to inhibit generation of unsaturated phospholipids is mirrored by the ability of PTX and other inventive compounds to inhibit proliferation and tumorogenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytes/macrophages is implicated in exacerbating or causing the disease. These include, for example, neurodegenerative diseases such as Alzheimer's disease, endotoxemia or toxic shock syndrome (Tracey et al., *Nature* 330:662, 1987 and Hinshaw et al., *Circ. Shock* 30:279, 1990); cachexia (Dezube et al., *Lancet* 355:662, 1990), and adult respiratory distress syndrome (Miller et al., *Lancet* 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., *N. Engl. J. Med.* 320:1585, 1989), chronic pulmonary inflammatory diseases such as silicosis and asbestosis (Piguet et al., *Nature* 344:245, 1990, and Bissonnette et al., *Inflammation* 13:329, 1989), and reperfusion injury (Vedder et al., *Proc. Natl. Acad. Sci. USA* 87:2643, 1990).

The compounds of the invention provide a mechanism to maintain homeostasis in cells contacted by primary stimuli through mitigating the effects of these primary stimuli on the secondary signaling pathways invoked within seconds of the primary stimulus. For example, administration of the inventive compounds in vivo or ex vivo provide a method to modify cellular behavior which method comprises contacting cells (in vivo or ex vivo) whose behavior is to be modified with an effective amount of an inventive compound or a pharmaceutical composition thereof wherein said method is: (1) a method to inhibit proliferation of tumor cells and said amount is sufficient to inhibit said proliferation; or (2) a method to promote differentiation of hematopoietic stem cells into red blood cells, platelets, lymphocytes, and granulocytes, and said amount is sufficient to promote said proliferation; or (3) a method to suppress activation of T-cells by antigen or IL-2 stimulation, and said amount is sufficient to promote said activation; or (4) a method to suppress activation of monocyte/macrophage cells by endotoxin, TNF, IL-1 or GM-CSF stimulation and said amount is sufficient to suppress said activation; or (5) a method to enhance the resistance of mesenchymal cells to the cytotoxic effect of tumor necrosis factor and said amount is sufficient to enhance said resistance; or (6) a method to suppress antibody production of B-cells in response to an antigen, IL-4 or CD40 ligand and said amount is sufficient to suppress said antibody production; or (7) a method to inhibit the proliferation of smooth muscle cells in response to growth factors capable of stimulating said proliferation and said amount is sufficient to inhibit said proliferation; or (8) a method to lower systemic vascular resistance conferred by endothelial cells and said amount is sufficient to reduce the release of hypertension-inducing substances; or (9) a method to lower systemic vascular resistance induced by endothelial cells and said amount is sufficient to enhance the release of anti-hypertensive substances; or (10) a method to lower expression of adhesion molecules induced by enhancers thereof, and said amount is sufficient to lower said expression; or (11) a method to suppress the activation of T-cells by HIV and said amount is sufficient to suppress said activation thus inhibiting viral replication; or (12) a method to inhibit the proliferation of kidney mesangial cells in response to stimulation by IL-1 and/or Mip-1α and/or PDGF and/or FGF and said amount is sufficient to inhibit said proliferation; or (13) a method to enhance the resistance of kidney glomerular or tubular cells to cyclosporin A or amphotericin B and said amount is sufficient to enhance said resistance; or (14) a method to prevent the suppression of growth stimulatory factor production in TNF-treated bone marrow stromal cells and said amount is sufficient to prevent said suppression; or (15) a method to prevent the release of mip-1α by IL-1, TNF, or endotoxin stimulated monocytes and macrophages; or (16) a method to prevent the release of platelet activating factor by IL-1, TNF, or endotoxin treated megakaryocytes, fibroblastic cells, and macrophages; or (17) a method to prevent the down-regulation of receptors for cytokines in TNF-treated hematopoietic progenitor cells and said amount is sufficient to prevent said down-regulation; or (18) a method to suppress the production of metalloproteases in IL-1-stimulated or TNF-stimulated glomerular epithelial cells or synovial cells and said amount is sufficient to enhance said production; or (19) a method to enhance the resistance of gastrointestinal or pulmonary epithelial cells to cytotoxic drugs or radiation and said amount is sufficient to enhance said resistance; or (20) a method to enhance the antitumor effect of a non-alkylating antitumor agent and said amount is sufficient to enhance said effect, or (21) a method to inhibit the production of osteoclast activating factor in response to IL-1, and said amount is sufficient to inhibit said production, or (22) a method to inhibit degranulation in response to IgE, and said amount is sufficient to inhibit said degranulation, or (23) a method to enhance the release of adrenergic neural transmitters, dopamine, norepinephrine, or epinephrine, or the neurotransmitter, acetylcholine, and said amount is sufficient to enhance said release, or (24) a method to modulate the post-synaptic "slow current" effects of the adrenergic neurotransmitters dopamine, epinephrine, or norepinephrine, or the neurotransmitter acetylcholine, and said amount is sufficient to modulate such slow currents.

The compounds of the invention can inhibit certain FGF (fibroblast growth factor) and PDGF (platelet derived growth factor) effects in vivo, such as inhibition of restenosis. For example, Ferns et al. (*Science* 253:1129, 1991) have shown that neointimal smooth muscle chemotaxis and angioplasty are inhibited in rats using a neutralizing antibody to PDGF. Also, Jawien et al. (*J. Clin Invest.* 89:507, 1992) have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., *Science* 248:1009, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., *Int. J. Cancer* 46:1066, 1990), metastatic melanoma cells (Yamanishi et al., *Cancer Res.* 52:5024, 1992), and glial tumors (Fleming et al., *Cancer Res.* 52:4550, 1992).

In Vitro Assays for Physiologic and Pharmacological Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000× g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 rain at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 µl complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 µCi/well of 40 to 60 Ci/mmole) and proliferation determined by liquid scintillation counting.

There are a series of in vitro assays that can be used to measure immunosuppressive activity of a particular compound. These assays are a predictive model for treatment or prevention of autoimmune diseases, such as diabetes, lupus, arthritis, and the like. A first assay measures immunosuppressive activity of a drug at the B cell level. Spleens from adult mice contain immature B cells that express surface IgM. Cross-linking the surface IgM with an anti-mu antibody results in B cell proliferation. Additionally, this activation results in an increased expression of interleukin-4 receptors(IL-4R) on the surface of such cells. IL-4 acts as a growth factor for B cells and will increase the amount of proliferation induced by anti-mu. In the first assay, a mixture of anti-mu and murine IL-4 is added to murine splenocytes to cause their proliferation. Mice spleens are obtained from adult mice and a single cell suspension is prepared in RPMI 1640 medium supplemented with 10% FCS. Cells (200,000) are plated into flat-bottomed wells and pre-incubated for 1–2 hrs with various concentrations of drug or PBS if it is a control well. A mixture of anti-mu and murine is added to the wells at a final concentration of 5 µg/ml anti-mu and 12.5 ng/ml IL-4 and plates are incubated for three days. Proliferation is determined on the third day with a pulse of tritiated thymidine. The IC50 concentration of a particular drug is the concentration of drug that results in a 50% inhibition of the proliferation obtained from the positive control.

A second immune suppression assay measures a T cell component to the immune reaction. Lymph nodes contain a mixture of cells including T cells, B cells and macrophages. Although the proliferating cells in this assay are T cells, the response is also dependent upon an antigen presenting cell such as a macrophage as well as an elaboration of various immunoregulatory cytokines. Murine T cells will proliferate in vitro in response to a soluble protein antigen if they are first primed with the antigen in vivo. In vivo priming involves emulsifying the antigen (chicken ovalbumin or OVA) in complete Freunds adjuvant and injecting 50 µg of OVA into both hind footpads of adult Balb/c mice. Fourteen days later the draining lymph nodes (popliteal) are removed and a single cell suspension is prepared in RPM1640 supplemented with 10% fetal calf serum. The lymph node cells (200,000) are plated into flat-bottom wells and OVA (200 µg/ml) and/or drug is added to appropriate wells and incubated for 5 days. Proliferation is determined and IC50's calculated as above.

A third assay measures an ability of an inventive compound to inhibit IL-2-induced proliferation of murine thymocytes. Thymus glands are obtained from 4–6 week old mice and plated as a single cell suspension into flat bottomed wells in RPMI 1640 medium supplemented with 10% fetal calf serum. The inventive compounds are added to appropriate wells and the cells are incubated for 1–2 hrs. Concanavilin A (ConA, 0.25 µg/ml) and IL-1 (20 ng/ml) are added and the plates are incubated for 4 days. Cell proliferation is determined as above. There are also variations for this assay that follow the same basic stimulation and measure inhibition of proliferation format. For example, splenocytes can be used instead of thymocytes to measure more of a B cell response than a T cell response (e.g., thymocytes) and stimulated by an anti-mu antibody (40 µg/ml), IL-4 or PMA (2.5 nM). Similarly, human lymphocytes can be used from normal human volunteers and stimulated with human IL-2 (100 U/ml, Genzyme) and/or anti-CD3 antibody (2.5 µg/ml, Boehinger Mannheim).

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability stain (e.g., 2',7'-bis-(2-carboroxyethyl)-5-(and -6)-carboxyfluorescein acetoxymethyl ester, BCECF excitation 488 nm and emission 525 nm) 24, 48 or 72 hours after addition of the drug.

Another assay for measuring activity of the inventive compounds involves determining PDGF (platelet derived growth factor) proliferative response using human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

One in vitro assay measures inhibition of the relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of an inventive compound at varying dosage levels.

Target cells include, for example, subcellular entities, such as, microsomes derived from mesenchymal and/or ectodermal cells, particularly microsomes from marrow stromal cells or human or rat mesangial cells; microsomes or synaptosomes derived from bovine brain; plasma membrane-enriched microsomes, plasma membranes derived as described in Bursten et al. (*J. Biol. Chem.* 226:20732–20743, 1991), or detergent-solubilized microsomes; synaptosomes, and membranes or other cell preparations solubilized using, for example, NP-40, Miranal, SDS or other neutral detergents; and detergent-solubilized, recombinant, or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, *Biochemistry* 30:6195–6203, 1991. A Rainin® mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

Some of the inventive compounds are effective for inhibiting yeast cell growth. This effect can be assayed by measuring growth of the yeast strain *Saccharomyces cervisiae*. A control yeast stain *Saccharomyces cervisiae* (BIO 101, Inc.) is grown overnight in YEPD broth at 30° C. An one to hundred dilution of the yeast culture is made with fresh YEPD broth. 100 μl Aliquots of the diluted culture are distributed into 96-wells titer plates. 100 μl Aliquots of drug is diluted in YEPD broth were then added to the wells. The titer plates are incubated at room temperature with continuous shaking. The cell density of the individual cultures are determined using a mircoplate reader with a A630 filter. The A630 of the individual yeast cultures are compared to control samples without adding drug. This assay is predictive of direct antimicrobial, particularly yeast and fungal, activity of the drugs studied.

A serotonin release assay is utilized to study the utility of the inventive compounds for treatment of asthma and allergy. This assay measures mast cell degranulation, which is an early phase reaction to allergen challenge. Mast cells grown in tissue culture are first loaded with $^3$H serotonin, which is incorporated into the granules in the cells. The mast cells are sensitized with antigen specific monoclonal IgE, and then triggered to degranulate with the specific antigen (dinitrophenol bound to BSA (DNP)). When the cells degranulate, $^3$H Serotonin is released into the medium, and can be measured directly. The ability of the inventive compounds to inhibit the degranulation response is determined by the decrease in $^3$H Serotonin released in the presence of drug and is represented as % INHIBITION. The IC50 of any given compound is determined by the ability of that compound to inhibit degranulation by 50%.

Specifically, the serotonin release assay seeds $2\times10^5$ cells in 0.5 ml medium in duplicate for spontaneous release, IgE+DNP, IgE+DNP+EtOH (vehicle control), and inventive compounds. One μCi [$^3_H$]-Serotonin/ml (i.e., 0.5 μCi/well) (NEN Research Products, cat. #NET-398 Hydroxytryptamine Binoxalate, 5-[1,2-$^3$H(N)]-(Serotonin Binoxalate, [1,2-$^3$H(N)]-)) and 1 μl/ml IgE is added. The cells are incubated for 18 hours at 37° C. in 5% $CO_2$, washed twice with 0.5 ml Isotonic Buffer (25 mM disodium PIPES pH 7.1,100 mM NaCl, 5 mM KCl, 5 mM glucose, 0.4 mM $MgCl_2$, 1 mM $CaCl_2$, 0.1% BSA), and sterile filtered. 250 μl Isotonic Buffer is added per well and the plates are equilibrated in an incubator for about 10 min. Drug is added and cells are activated with 40 ng/ml DNP-BSA (1 mg/ml Diluted 1:200 in Isotonic Buffer) for 45 minutes using 2 μl/250 μl. Spontaneous release is determined in incubated cells with 250 μl Isotonic Buffer for 45 minutes and the reaction is stopped by removing supernatant and centrifuging at ~4000 rpm in microfuge for 15 seconds to remove any detached cells. Released radiolableled serotonin is counted. To determine amount of $^3$H-serotonin incorporated into the cells, (a) remove Isotonic Buffer and lyse cells by adding 250 μl 1% Triton-X100 in PBS, (b) add to 5 ml scintillation fluid, (c) wash 2× with Triton/PBS, and (d) add washes to scintillation tube. Percent serotonin release is calculated by dividing the amount of released serotonin by the sum of incorporated plus released serotonin and correcting for spontaneous released serotonin. Compound inhibition is calculated by dividing the percent serotonin release in the presence of a compound by the percent serotonin release in the absence of the compound.

An ex vivo human sepsis model is described in Desch et al., *Lymphokine Res.* 8:141, 1989 and in Ooi et al., *J. Exp. Med.* 174:649, 1991. Briefly, whole blood from humans is incubated with LPS (endotoxin). TNF released from cells (mostly from monocytes) is measured. The inventive compounds lower TNF levels as compared with untreated controls in this model.

Compounds of the Invention

We have found that the compounds described herein can be used to maintain homeostasis of a large variety of target cells in response to a variety of stimuli. In addition, the inventive compounds and compositions are suitable for normal routes of therapeutic administration and permit effective dosages to be provided.

The invention is directed to the use of a class of halogen, isothionate or azide substituted compounds, preferably heterocycloic compounds. The inventive compounds are effective in modulating cellular response to external or in situ primary stimuli, as well as to specific modes of administration of such compounds in effective amounts.

The present invention provides compounds and pharmaceutical compositions comprising a compound having the formula:

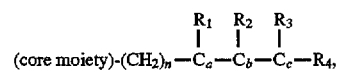

wherein n is an integer from 5 to 9, wherein the core moiety comprises at least one five to seven-membered ring or an open chain analog of such a ring group, wherein $C_a$, $C_b$, and $C_c$ are an R or S enantiomer or racemic mixture and the $C_a$, $C_b$, and $C_c$ carbon atoms are bonded together by a single bond, double bond, ether or ester linkages, wherein $R_1$, $R_2$ and $R_3$ are independently halo, hydroxy, hydrogen, keto, isothiocyano, azide or haloacetoxy with the proviso that at least one of $R_1$, $R_2$ or $R_3$ must be a halo, isothiocyano, azide or haloacetoxy group, wherein $R_4$ is hydrogen, $C_{1-6}$ alkyl, $C_{1-6}$ alkenyl, cyclo $C_{4-6}$ alkyl, or phenyl, and wherein halo refers to fluoro, chloro, bromo and iodo.

Preferably, one of $R_1$, $R_2$ and $R_3$ is a hydrogen (most preferably $R_2$), and $R_1$ and $R_3$ are independently a halo (most preferably a chloro or fluoro) and a keto or a hydroxy group, and n is preferably an integer from 5–6. Most preferably, the compound is R and S enantiomers and racemic mixtures of compounds selected from the group consisting of 1-(5-isothiocyanatohexyl)3,7-dimethylxanthine (CT2519), 1-(6-chloro-5-oxohexyl)3,7-dimethylxanthine (CT1595), 1-(6-azidohexyl)3,7-dimethylxanthine (CT2557), 1-(9-acetoxy-10-bromodecyl) 3,7-dimethylxanthine (CT1583), 1-(5-fluorohexyl)3,7-dimethylxanthine (CT1577), 1-[5-(chloroacetoxy)hexyl]3,7-dimethylxanthine (CT1529), 1-[6-(chloroacetoxy)hexyl] 3,7-dimethylxanthine (CT1527), 1-(6-chlorohexyl)3,7-dimethylxanthine (CT1525), 1-(6-azido-5-hydroxyhexyl)3,7-dimethylxanthine (CT1517), 1-(7-acetoxy-8-bromooctyl) 3,7-dimethylxanthine (CT1514), 1-(5-acetoxy-6-bromohexyl)-3-methylbenzoyleneurea (CT1205), 3-(8-acetoxy-9-bromononyl)-1-methyluracil (CT1801), and 3-(8-acetoxy-9-bromononyl)-1-methylthymine (CT1908).

Preferably, the core moiety has from one to three, five to six membered ring structures in a predominantly planar structure. Preferably, the halogen, isothiocyanate or azide substituent is bonded to a ring nitrogen if one exists.

For example, the core moiety is selected from the group consisting of xanthine, halogen-substituted xanthines, 3,7-dimethylxanthine, 3-methylxanthine, 3-methyl-7-methylpivaloylxanthine, 8-amino-3-methylxanthine, 7-methylhypoxanthine, 1-methyluracil, 1-methylthymine, 1-methyl-5,6-dihydrouracil, glutarimides, phthalimide, 1-methyl-2,4(1H,3H)-quinazolinedione (1-methylbenzoyleneurea), 6-aminouracil, homophthalimide, succinimide, 1,3-cyclohexanedione, resorcinol, 1,3-dihydroxynaphthalene, 1,3-cyclopentanedione, 1,3-dimethyldihydroxypyrazolo[4,3-d]pyrimidine, 5-substituted uracils, 6-substituted uracils, 1-methylpyrrolo [2,3-d]pyrimidine, 1-methyllumazine, imidazole amides, 2-pyrrole amides, 3-pyrrole amides, benzamides, methylbarbituric acid, benzene, piperdine, delta-lactam, 2-hydroxypyridine, 1,2,3,4-tetrahydroisoquinolone, isocarbostyril, and quinazolin-4 (3H)-one. Most preferably, the heterocyclic core is a xanthine. The core moiety can also include a non-cyclic group. Examples of non-cyclic core groups include open chain analogs of glutarimide, carboxylic acid, a hydroxyl group, sulfone, sulfonate, and the like.

The present invention further provides a pharmaceutical composition comprising an inventive compound or a salt thereof and a pharmaceutically acceptable excipient, wherein the pharmaceutical composition is formulated for oral, parenteral or topical administration to a patient.

The present invention further provides a pharmaceutical composition comprising an inventive compound and a pharmaceutically acceptable excipient, wherein the pharmaceutical composition is formulated for oral, parenteral or topical administration to a patient.

The present invention further comprises a pharmaceutical composition comprising one or a plurality of inventive compounds and a pharmaceutically acceptable carrier or excipient. The individuals to be treated with an inventive compound or inventive pharmaceutical composition may either be contacted with the compound of the invention in vitro culture, in an extracorporeal treatment, or by administering (oral, parenteral or topical) the compound of the invention or pharmaceutical composition to a subject whose cells are to be treated.

Illustrative compounds of the invention include both R and S enantiomers and racemic mixtures of the following compounds:

TABLE 1

| | |
|---|---|
| CT2519 | 1-(5-isothiocyanatohexyl)theobromine |
| CT1595 | 1-(6-chloro-5-oxohexyl)theobromine |
| CT2557 | 1-(6-azidohexyl)theobromine |
| CT1583 | 1-(9-acetoxy-10-bromodecyl)theobromine |
| CT1577 | 1-(5-fluorohexyl)theobromine |
| CT1529 | 1-[5-(chloroacetoxy)hexyl]theobromine |
| CT1527 | 1-[6-(chloroacetoxy)hexyl]theobromine |
| CT1525 | 1-(6-chlorohexyl)theobromine |
| CT1517 | 1-(6-azido-5-hydroxyhexyl)theobromine |
| CT1514 | 1-(7-acetoxy-8-bromooctyl)theobromine |
| CT1205 | 1-(5-acetoxy-6-bromohexyl)-3-methylbenzoyleneurea |
| CT1801 | 3-(8-acetoxy-9-bromononyl)-1-methyluracil |
| CT1908 | 3-(8-acetoxy-9-bromononyl)-1-methylthymine |

Coadministration With a P-450 Inhibitor

The coadministration in vivo of the compounds of the invention along with an inhibitor of P-450 results in an enhanced effect due to a longer half life of the inventive compounds. This in vivo effect is due to inhibition of a degradation pathway for the compounds of the invention; in particular, dealkylation at the N7 position of the xanthine ring. For example, NIH3T3-D5C3 cells can be used to compare effects of an inventive compound alone or in combination with a P-450 inhibitor by comparing transformation phenotype control, incubation with an inventive compound alone, and coincubation of an inventive compound with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gm, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof, calculated as the free base.

The inventive compounds may be administered orally. The daily dosage regimen for oral administration is suitably from about 0.1 mg/kg to about 1000 mg/kg per day. For administration the dosage is suitably form about 0.001 mg/kg to about 40 mg/kg of the inventive compound or a pharmaceutically acceptable salt thereof calculated as the free base. The active ingredient may be administered from 1 to 6 times a day, sufficient to exhibit activity.

The inventive compounds may be administered by inhalation (e.g., intranasal or oral) Appropriate dosage forms include an aerosol or a metered dose inhaler, as prepared by conventional techniques. The daily dosage is suitably form about 0.001 mg/kg to about 40 mg/kg of the inventive compound or a pharmaceutically acceptable salt thereof, calculated as the free base. Typical compounds for inhalation are in the form of a solution, suspension or emulsion that may be administered as a dry powder or in the form of an aerosol using a conventional propellant.

The invention is illustrated by the following examples which should not be regarded as limiting the invention in any way. In these examples PTX means pentoxifylline.

EXAMPLE 1

This example illustrates the synthesis of several compounds that are used as intermediates for the synthesis of other compounds.

1-(5,6-Oxidohexyl)-3,7-dimethylxanthine (CT1541) was synthesized and used as an intermediate for synthesizing CT1517 and CT1595 as described in examples 2 and 3 below. A mixture of 1-bromo-5-hexene (10.7 g, 66 mmol), sodium hydride (1.58 g, 66 mmol), and theobromine (11.9 g, 66 mmol) in dimethylsulfoxide (100 ml) was stirred for 43 hr. The solution was treated with water (200 ml) and then extracted with dichloromethane (3×80 ml). The combined extracts were washed with water (3×100 ml), dried over magnesium sulfate, and then the solvent was evaporated under vacuum to give 1-(5-hexenyl)-3,7-dimethylxanthine (CT1539) (17 g, 98% yield) as a white powder.

To 1-(5-hexenyl)-3,7-dimethylxanthine (CT1539) (1.07 g, 4.1 mmol) and 4-methylmorpholine-N-oxide (1.44 g, 12.3 mmol) in water (20 ml) and acetone (10 ml) was added 2.5% solution of osmium tetraoxide in t-butanol (6 drops). After stirring for 48 hr, the mixture was treated with 20% aqueous sodium dithionite solution (20 ml). After 2 min, the mixture was extracted with 25% ethanol-dichloromethane (3×30 ml). The combined extracts were dried over magnesium sulfate and the solvents were evaporated under vacuum to give 1-(5,6-dihydroxyhexyl)-3,7-dimethylxanthine (CT1502) (750 mg, 62% yield) as a white powder.

To 1-(5,6-dihydroxyhexyl)-3,7-dimethylxanthine (CT1502) (1.0 g, 3.38mmol) was added 30% hydrogen bromide-acetic acid (3.4 ml) over 30 sec and then stirred until all of the solid had dissolved (2.5 hr). The solution was poured carefully over a mixture of sodium bicarbonate (12 gm) and ice water (50 ml). After carbon dioxide evolution had subsided, the mixture was extracted with dichloromethane (3×25 ml). The combined extracts were dried over magnesium sulfate and the solvent was evaporated under vacuum to give 1-(5-acetoxy-6-bromohexyl)-3,7-dimethylxanthine (1.3 g, 96% yield) as a viscous oil which was dissolved in methanol (5 ml). A 1M solution of sodium methoxide in methanol (3.9 ml) was added over 30 sec. After stirring for 20 min, the solution was treated with water (20 ml) and then extracted with dichloromethane (3×15 ml). The combined extracts were dried over magnesium sulfate and the solvents were evaporated under vacuum to give 1-(5,6-oxidohexyl)-3,7-dimethylxanthine (CT1541) (900 mg, 100% yield) as white crystals.

1-(6-Hydroxyhexyl)-3,7-dimethylxanthine (CT1556) was used as an intermediate for the synthesis of CT1525 (example 4), CT1527 (example 5), and CT1589 (example 6). A mixture of theobromine (1.0 g, 5.5 mmol) and 50% sodium hydride in oil (264 mg, 5.5 mmol) in dimethylsulfoxide (20 ml) was stirred for 50 min and then 6-bromo-1-hexanol (1.0 g, 5.5 mmol) was added. After stirring for 18 hr, the solution was treated with water (50 ml) and then extracted with hexane (2×25 ml). The aqueous phase was extracted with 25% ethanol-dichloromethane (3×35 ml). The combined ethanol-dichloromethane extracts were dried over magnesium sulfate and then the solvents were evaporated under vacuum. The remaining dimethylsulfoxide was removed by distillation under full pump vacuum to give 1-(6-Hydroxyhexyl)-3,7-dimethylxanthine (CT1556) (1.4 g, 91% yield) as a white powder.

1-(5-Hydroxyhexyl)-3,7-dimethylxanthine (CT1501 ) was used as an intermediate for the synthesis of CT1529 (example 7) and CT1577 (example 8). To a solution of 1-(5,6-oxohexyl)-3,7-dimethylxanthine (CT1541) (250 mg, 0.9 mmol) (made as an intermediate and described in this example) in absolute ethanol (15 ml) was added sodium borohydride (85 mg, 2.25 mmol) and heated at 90° C. for 2 hr. After cooling to ambient temperature, the solution was treated with half-saturated aqueous ammonium chloride solution (30 ml). The mixture was extracted with 25% ethanol-dichloromethane (4×15 ml). The combined extracts were dried over magnesium sulfate and the solvents were evaporated under vacuum to give 1-(5-hydroxyhexyl)-3,7-dimethylxanthine (CT1501) (250 mg, 100% yield).

3-(5,6-Dihydroxyhexyl)-1-methylbenzoyleneurea (CT1204) was used as an intermediate for the synthesis of CT1205 (example 10). A solution of sodium hydride (0.76 g, 30 mmol) and benzoyleneurea (4.86 g, 30 mmol) in dimethylsulfoxide (100 ml) was stirred for 10 min and then methyl iodide (1.87 ml, 30 mmol) was added. After stirring for 14 hr, water (100 ml) was added and the solution was extracted with dichloromethane (3×100 ml). The mixture was filtered and the dichloromethane phase was dried over sodium sulfate. After evaporation of the solvent under vacuum, the residue was recrystallized (dichloromethane) to give 1-methylbenzoyleneurea (CT1201) (1.3 g, 25% yield) as a white solid.

A solution of sodium hydride (0.17 g, 6.8 mmol) and 1-methylbenzoyleneurea (CT1201) (1.07 g, 6.1 mmol) in dimethyl sulfoxide (50 ml)was stirred for 10 min and then 1-bromohexene (0.82 ml, 6.8 mmol) was added. After 14 hr, water (50 ml) was added and the solution was extracted with dichloromethane (3×30 ml). The combined organic phases were washed with water (3×50 ml), dried over sodium sulfate, and the solvent was evaporated under vacuum to give 3-(5-hexenyl)-1-methylbenzoyleneurea (CT1203) (1.51 g, 96%) as a white solid.

A solution of 3-(5-hexenyl)-1-methylbenzoyleneurea (CT1203) (1.5 g, 5.8 mmol), 4-methylmorphline-N-oxide (0.87 g, 7.4 mmol), and potassium osmate(IV) dihydrate (0.021 g, 0.1 mmol) in acetone (12.5 ml) water (4 ml) was stirred. After 18 hr, a 20% aqueous solution hydrosulfite (20 ml) was added and stirred for 30 min. The solution was extracted with dichloromethane (3×75 ml). The combined organic phases were dried over sodium sulfate and the solvent was evaporated under vacuum. The residue was purified by flash chromatography (silica, 5% methanol-dichloromethane) to give 3-(5,6-dihydroxyhexyl)-1-methylbenzoyleneurea (CT1204) (1.59 g, 94%) as a white solid.

3-(8,9-Dihydroxynonyl)-1-methyluracil (CT1818) was synthesized as an intermediate for CT1801 (example 11). A mixture of sodium hydride (365 mg, 16 mmol) and 1-methyluracil (2.00 g, 16 mmol) in dimethyl sulfoxide (40 ml) was stirred for 15 min and then 6-bromo-1-nonene (3.26 g, 16 mmol) was added. After stirring for 16 hr, the mixture was poured into water (50 ml) and the mixture was extracted with dichloromethane (3×60 ml). The combined organic layers were washed with water (50 ml), with saturated aqueous sodium chloride solution (30 ml), and dried over sodium sulfate. The solvent was evaporated under vacuum to give 1-methyl-3-(8,9-nonenyl)uracil (CT1817) (3.72 g, 94% yield) as a colorless oil which solidified upon standing.

A solution of 3-(8,9-nonenyl)-1-methyluracil (CT1817) (3.72 g, 15 mmol), 4-methylmorpholine-N oxide (2.10 g, 18 mmol), and potassium osmate (IV) dihydrate (11 mg, 3.0× $10^{-5}$ mmol) in acetone (20 ml) and water (10 ml) was stirred for 2 days. After addition of sodium hydrosulfite (100 mg), the mixture was extracted with dichloromethane (4×50 ml). The combined organic layers were dried over sodium sulfate and the solvent was evaporated to a residue which was crystallized (ether-dichloromethane) to give 3-(8,9-dihydroxynonyl)-1-methyluracil (CT1818) (2.66 g, 63% yield) as white crystals.

3-(8,9-Dihydroxynonyl)-1-methylthymine (CT1918) was used as an intermediate for the synthesis of CT1908 (example 12). A mixture of sodium hydride (343 mg, 14 mmol) and 1-methylthymine (2.00 g, 14 mmol) in dimethylsulfoxide (40 ml) was stirred for 15 min and then 9-bromo-1-nonene (2.93 g, 14 mmol) was added. After stirring for 20 hr, the mixture was poured into water (40 ml) and extracted with dichloromethane (3×50 ml). The combined organic layers were washed with water (40 ml), with saturated aqueous sodium chloride solution (20 ml), and dried over sodium sulfate. The solvent was evaporated to give 3-(8-nonenyl)-1-methylthymine (CT1917) (2.76 g, 73% yield) as a colorless oil which solidified upon standing.

A solution of 3-(8-nonenyl)-1-methylthymine (CT1917) (2.63 g, 9.9 mmol), 4-methylmorpholine-N oxide (1.39 g, 12 mmol), and potassium osmate (IV) dihydrate (7 mg, 2×$10^{-5}$ mmol) in acetone (20 ml) and water (10 ml) was stirred for 18 hr. After addition of saturated aqueous sodium hydrosulfite solution (10 ml), and stirring for 15 min, the mixture was extracted with 20% methanol-dichloromethane (2×50 ml). The combined organic layers were washed with water (15 ml), with saturated aqueous sodium chloride solution (15 ml), and dried over sodium sulfate. The solvent was evaporated under vacuum to give a solid which was recrystallized (ethanol) to give 3-(8,9-dihydroxynonyl)-1-methylthymine (CT1918) (2.68 g, 91% yield).

5-Aminohexyl-3,7-dimethylxanthine (CT1520) were used as an intermediate for the synthesis of CT2519 (example 13). To a solution of pentoxifylline (1.39 g, 5 mmol) and ammonium acetate (3.85 g, 50 mmol) in methanol (50 ml) was added sodium cyanoborohydride (628 mg, 10 mmol). After stirring for 24 h, the mixture was treated with dichloromethane (50 ml) and water (50 ml). The aqueous layer was treated with saturated aqueous ammonium chloride solution (20 ml) and stirred for 15 min. After treatment with 30% aqueous ammonium hydroxide solution (30 ml), the solution was extracted with 25% ethanol-dichloromethane (3×35 ml). The combined extracts were dried over magnesium sulfate and then the solvents were evaporated under vacuum to give 5-aminohexyl-3,7-dimethylxanthine (CT1520) (950 mg, 68% yield).

1-(9,10-Dihydroxydecyl)-3,7-dimethylxanthine (CT1564) was used as an intermediate for the synthesis of CT1583 (example 14). To a solution of 9-decene-1-ol (3.0 g, 19.2 mmol) in dichloromethane (100 ml) at 0° C. was added methanesulfonyl chloride (2.20 g, 19.2 mmol) followed by triethylamine (2.91 g, 28.8 mmol) After stirring for 15 min at 0° C., the reaction was allowed to warm to room temp. After stirring for 2 hr, the reaction was poured into water (100 ml) and extracted with dichloromethane (3×60 ml). The combined organic layers were dried over sodium sulfate and the volatiles were evaporated under vacuum to give 9-decene-1-methanesulfonate (4.52 g, 100% yield) which was used without further purification. To a suspension of sodium hydride (461 mg, 19.2 mmol) in dimethylsulfoxide (30 ml) was added theobromine (3.45 g, 19.2 mmol). After stirring for 15 min, 9-decene-1-methanesulfonate (2.25 g, 11 mmol) was added and the mixture was stirred at room temperature for 18 hr and then at 100° C. for 40 min. After cooling to ambient temperature, the mixture was poured into water (100 ml) and extracted with dichloromethane (3×50 ml). The combined organic layers were washed with saturated aqueous sodium chloride solution (60 ml) and dried over magnesium sulfate. The solvent was evaporated under vacuum to give a solid which was recrystallized (ether) to give 1-(9-decenyl)-3,7-dimethylxanthine (CT1563) (3.40 g, 56% yield).

A solution of 1-(9-decenyl)-3,7-dimethylxanthine (CT1563) (3.2g, 10.1 mmol), 4-methylmorpholine-N-oxide (1.41 g, 12 mmol) and 2.5% osmium tetraoxide in t-butanol (3 drops) in acetone (40 ml) and water (10 ml) was stirred for 24 hr. After the addition of saturated sodium dithionite solution (5 ml) the mixture was stirred for 15 min. The mixture was extracted with 25% ethanol-dichloromethane (4×50 ml). The combined organic layers were dried over sodium sulfate and the solvents were evaporated under vacuum to a give solid which was recrystallized (ethanol) to give 1-(9,10-dihydroxydecyl)-3,7-dimethylxanthine (CT1564) (3.30 g, 93% yield).

1-(7,8-Dihydroxyoctyl)-3,7-dimethylxanthine (CT1538) was used as an intermediate for the synthesis of CT1514 (example 15). To a suspension of sodium hydride (580 mg, 24.2 mmol) in dimethylsulfoxide (100 ml) was added theobromine (3.96 g, 22.0 mmol). After stirring for 30 min, 8-bromo-1-octene (3.96 g, 22 mmol) was added and the mixture was stirred for 16 hr. The mixture was poured into water (200 ml) and extracted with dichloromethane (3×50 ml). The combined organic layers were washed with saturated aqueous sodium chloride solution (50 ml), dried over sodium sulfate, and the solvent was evaporated under vacuum to give 1-(7-octenyl)-3,7-dimethylxanthine (CT1535) (6.22 g, 97% yield) as an oil which solidified upon standing.

A solution of 1-(7-octenyl)-3,7-dimethylxanthine (CT1535) (1.00 g, 4.5 mmol), 4-methylmorpholine-N oxide (553 mg, 4.7 mmol), and 2.5% osmium tetroxide in t-butanol (3 drops) in acetone (25 ml) and water (20 ml) was stirred for 4 days. After addition of saturated aqueous sodium hydrosulfite solution (10 ml), the mixture was stirred for 30 min and water (50 ml) was added. The mixture was extracted with 20% ethanol-dichloromethane (3×50 ml) and the solvents were evaporated under vacuum to give a solid which was recrystallized (ethanol) to give 1-(7,8-dihydroxyoctyl)-3,7-dimethylxanthine (CT1538) (726 mg, 63% yield) as a white solid.

EXAMPLE 2

This example illustrates a method for synthesis of 1-(6-azido-5-hydroxyhexyl)-3,7-dimethylxanthine (CT1517). A mixture of (5,6-Oxidohexyl)-3,7-dimethylxanthine (CT1541) (1.00 g, 3.6 mmol) and sodium azide (818 mg, 12.6 mmol) in acetone (10 ml) and water (10 ml) was refluxed for 5 hr. After cooling to ambient temperature the mixture was poured into water (10 ml) and extracted with chloroform (3×30 ml). The combined organic layers were washed with water (20 ml) and saturated aqueous sodium chloride solution (20 ml) and then dried over sodium sulfate. After evaporation of the solvents under vacuum, the solid was recrystallized (chloroform-ethyl ether) to give 1-(6-azido-5-hydroxyhexyl)-3,7-dimethylxanthine (CT1517) (617 mg, 53 % yield).

EXAMPLE 3

This example illustrates the synthesis of 1-(6-chloro-5-oxohexyl)-3,7-dimethylxanthine (CT1595). To a solution of dimethylsulfoxide (0.390 g, 5.00 mmol) in dichloromethane (20 ml), at −60° C., was added oxalyl chloride (0.634 g, 5.00 mmol). After stirring for 5 min, 1-(5,6-oxidohexyl)-3,7-dimethylxanthine (CT1541 ) (0.548 g, 2.00 mmol) and methanol (0.0064 g, 0.20 mmol) were added. After stirring for 30 min at −60° C., triethylamine (1.01 g, 10.0 mmol) was added. After stirring at −60° C. for 10 min, the mixture was warmed to 25° C. over 30 min and then washed with saturated aqueous ammonium chloride solution (30 ml), with water (30 ml), and with saturated aqueous sodium chloride solution (30 ml). The organic phase was dried over magnesium sulfate and the solvent was evaporated under vacuum to give a residue which was purified by chromatography (silica, methanol-dichloromethane) to afford CT1595 (0.38 g, 62%yield) as a cream solid.

EXAMPLE 4

This example illustrates the synthesis of 1-(6-chlorohexyl)-3,7-dimethylxanthine (CT1525). A solution of 1-(6-hydroxyhexyl)-3,7-dimethylxanthine (CT1556) (1 g, 3.6 mmol) and triphenylphosphine (1.2 g, 4.6 mmol) in carbon tetrachloride (20 ml) was refluxed for 12 hr. The excess carbon tetrachloride was evaporated under reduced pressure. The crude product was purified by flash chromatography (silica gel, 40% hexane-ethylacetate) to give 1-(6-chlorohexyl)-3,7-dimethylxanthine (CT1525) (0.56 g, 53% yield).

EXAMPLE 5

This example illustrates the synthesis of 1-(6-(chloroacetoxy)hexyl)-3,7-dimethylxanthine (CT1527). A solution of the chloroacetyl chloride (339 mg, 3 mmol) in dichloromethane (5 ml) was added dropwise at 0° C. to a solution of 1-(6-hydroxyhexyl)-3,7-dimethylxanthine (CT1556) (560 mg, 2 mmol) and triethylamine (607.2 mg, 6 mmol) in dichloromethane (5 ml). After warming to ambient temperature, the mixture was stirred for 12 hr and then saturated aqueous sodium bicarbonate solution (5 ml) was added. The mixture was extracted with dichloromethane (3×50 ml). The combined organic extracts was washed with 1% aqueous hydrogen chloride (15 ml), with water (15 ml), and with saturated sodium chloride solution (15 ml). After drying over magnesium sulfate, the solvent was evaporated under vacuum. The residue was purified by flash chromatography (silica gel, 20% hexane-ethyl acetate) to give 1-(6-(chloroacetoxy)hexyl)-3,7-dimethylxanthine (CT1527) (296 mg, 50% yield).

EXAMPLE 6

This example illustrates the synthesis of 1-(6-bromohexyl)-3,7-dimethylxanthine (CT1589). Triphenylphosphine (1.2 g, 4.6 mmol) was added in portions to a solution of 1-(6-hydroxyhexyl)-3,7-dimethylxanthine (CT1556) (1 g, 3.6 mmol) and carbon tetrabromide (1.52 g; 4.6 mmol) in dichloromethane. After stirring for 30 minutes, the solvent was evaporated under reduced pressure. The crude product was purified by flash chromatography (silica gel, 40% hexane-ethyl acetate) to give 1-(6-bromohexyl)-3, 7-dimethylxanthine (CT1589) (0.70 g, 59% yield).

EXAMPLE 7

This example illustrates the synthesis of 1-(5-(chloroacetoxy)hexyl)-3,7-dimethylxanthine (CT1529). To a solution of the 1-(5-hydroxyhexyl)-3,7-dimethylxanthine (CT1501) (1.12 g, 4 mmol) and triethylamine (809.6 mg; 8 mmol) in dichloromethane (10 ml) was added a solution of the chloroacetyl chloride (678 mg; 3 mmol) in dichloromethane (10 ml) dropwise at 0° C. After warming to ambient temperature and stirring overnight, saturated aqueous sodium bicarbonate solution (10 ml) was added and the mixture was extracted with dichloromethane (3×75 ml). The combined organic extracts were washed with 1% aqueous hydrogen chloride (30 ml), with water (30 ml), and with saturated sodium chloride solution (30 ml). After drying over magnesium sulfate, the solvent was evaporated under reduced pressure. The residue was purified by flash chromatography (silica gel, 20% hexane-ethyl acetate) to give 1-(5-(chloroacetoxy)hexyl)-3,7-dimethylxanthine (CT1529) (560 mg, 49% yield).

EXAMPLE 8

This example illustrates the synthesis of 1-(5-fluorohexyl)-3,7-dimethylxanthine (CT1577). A mixture of 1-(5- hydroxyhexyl)-3,7-dimethylxanthine (CT1501) and 70% hydrogen fluoride-pyridine solution in a polypropylene bottle was heated at 40°–50° C. for 20 hr. After cooling to ambient temperature, saturated aqueous sodium bicarbonate solution (50 ml) was added. The mixture was extracted with dichloromethane (3×40 ml) and the combined extracts were dried over sodium sulfate. After evaporation of the solvent under a stream of nitrogen, the residue was purified by chromatography (silica, ethyl acetate) to give 1-(5-fluorohexyl)-3,7-dimethylxanthine (CT1577) (150, 21% yield).

EXAMPLE 9

This example illustrates the synthesis of 1-(6-azidohexyl)-3,7-dimethylxanthine (CT2557). To a stirred mixture of 1-(6-bromohexyl)-3,7-dimethylxanthine (CT1589, from example 6 herein) (115 mg, 0.33 mmol) and 25% aqueous solution of sodium azide (42.9 mg, 0.66 mmol) was added etrabutylammonium bromide (5.3 mg, 0.0165 mmol). After heating at 100° C. for 12 hr, the mixture was cooled to room temperature and then extracted with dichloromethane (3×50 ml). The combined organic extracts was washed with saturated aqueous sodium chloride solution (50 ml), dried over magnesium sulfate, and concentrated under reduced pressure. The residue was purified by flash chromatography (silica, ethyl acetate) to give 1-(6-azidohexyl)-3,7-dimethylxanthine (CT2557) (80 mg, 88% yield)

EXAMPLE 10

This example illustrates the synthesis of 3-(5-acetoxy-6-bromohexyl)-1-methylbenzoyleneurea (CT1205). A mixture of 3-(5,6-dihydroxyhexyl)-1-methylbenzoyleneurea (CT1204) (0.92 g, 3.1 mmol) and 30% hydrogen bromide-acetic acid (0.63 ml, 9.3 mmol) was stirred for 90 min. The solution was poured into a stirred mixture of sodium bicarbonate (0.78 g, 9.3 mmol), water (20 ml), and dichloromethane (20 ml). The phases were separated and the aqueous phase was extracted with dichloromethane (2×20 ml). The combined organic phases were washed with saturated aqueous sodium chloride solution (20 ml), dried over sodium sulfate, and the solvent was evaporated under vacuum to give 1-(5-acetoxy-6-bromohexyl)-3-methylbenzoyleneurea (CT1205) (1.2 g, 96% yield).

EXAMPLE 11

This example illustrates the synthesis of 3-(8-acetoxy-9-bromononyl)-1-methyluracil (CT1801). A mixture of 3-(8,9-dihydroxynonyl)-1-methyluracil (CT1818) (2.15 g, 7.6 mmol) and 30% hydrogen bromide-acetic acid (4.5 ml, 23 mmol) was stirred for 6 hr. The solution was added slowly to a well stirred mixture of sodium bicarbonate (8.4 g, 0.1 mmol), water (30 ml), and dichloromethane (30 ml). The layers were separated and the aqueous layer extracted with dichloromethane (3×40 ml). The combined organic layers were washed with saturated aqueous sodium chloride solution (20 ml) and dried over sodium sulfate. The solvent was evaporated under vacuum to give 3-(8-acetoxy-9-bromononyl)-1-methyluracil (CT1801) (2.89 g, 97% yield).

EXAMPLE 12

This example illustrates the synthesis of 3-(8-acetoxy-9-bromononyl)-1-methylthymine (CT1908). A mixture of 3-(8,9-dihydroxynonyl)-1-methylthymine (CT1918) (2.16 g, 7.6 mmol) and 30% hydrogen bromide-acetic acid (4.5 ml, 23 mmol) was stirred for 1 hr. The reaction was added slowly to a well stirred mixture of sodium bicarbonate (8.4 g, 0.1 mmol), ice water (30 ml), and dichloromethane (30 ml). The layers were separated and the aqueous layer extracted with dichloromethane (2×60 ml). The combined organic layers were with water (30 ml), with saturated aqueous sodium chloride solution (30 ml), and then dried over sodium sulfate. The solvent was evaporated under vacuum to give 3-(8-acetoxy-9-bromononyl)-1-methylthymine (CT1908) (2.59 g, 85% yield).

EXAMPLE 13

This example illustrates the synthesis of 1-(5-isothiocyanatohexyl)-3,7-dimethylxanthine (CT2519). To a solution of 1-(5-aminohexyl)-3,7-dimethylxanthine (CT1520) (0.2 g, 0.7 mmol), sodium bicarbonate (0.24 g, 2.8 mmol), and dichloromethane (2 ml) was added thiophosgene (0.081 ml, 1.1 mmol) dropwise. After stirring for 18 hr, the reaction mixture was poured into 15% aqueous ammonium hydroxide solution (15 ml). After stirring for 20 min, the solution was extracted with dichloromethane (3×15 ml). The combined organic phases were dried over sodium sulfate and the solvent was evaporated under vacuum 1-(5-isothiocyanatohexyl)-3,7-dimethylxanthine (CT2519) (0.21 g, 91% yield) as a white solid.

EXAMPLE 14

This example illustrates the synthesis of 1-(9-acetoxy-10-bromodecyl)-3,7-dimethylxanthine (CT1583). A mixture of 1-(9,10-dihydroxydecyl)-3,7-dimethylxanthine (CT1564) (2.11 g, 6 mmol) and 30% hydrogen bromide-acetic acid (3.6 ml, 18 mmol) was stirred for 90 min. The solution was poured into a mixture of sodium bicarbonate (5 g), water (40 ml), and dichloromethane (50 ml). After 10 min of vigorous stirring, the layers were separated and the aqueous layer was extracted with dichloromethane (2×50 ml). The combined organic layers were dried over sodium sulfate and the solvent was evaporated under vacuum to give 1-(9-acetoxy-10-bromodecyl)-3,7-dimethylxanthine (CT1583) (2.72 g, 100% yield).

EXAMPLE 15

This example illustrates the synthesis of 1-(7-acetoxy-8-bromooctyl)-3,7-dimethylxanthine (CT1514). A mixture of 1-(7,8-dihydroxyoctyl)-3,7-dimethylxanthine CT1538 (2.11 g, 6 mmol) and 30% hydrogen bromide-acetic acid (3.58 ml, 18 mmol) was stirred for 90 min. The solution was poured into a well stirred mixture of sodium bicarbonate (4 g), water (50 ml), and dichloromethane (30 ml). After 10 min of vigorous stirring the layers were separated and the aqueous layer was extracted with dichloromethane (2×50 ml). The combined organic layers were dried over sodium sulfate) and the solvent was evaporated under vacuum to give 1-(7-acetoxy-8-bromooctyl)-3,7-dimethylxanthine (CT1514) (2.51 g, 94% yield).

EXAMPLE 16

This example illustrates data regarding proliferative activity of various inventive compounds for inducting CMV promoter activity. The CMV promoter assay measures gene transcription and translation activity wherein any active compounds will nave cytotoxic activity to inhibit cellular protein synthesis machinery in transformed (adenovirus) cells. Each compound was tested and the data is listed in Table 2 below. CT2519 was the most cytotoxic compound tested.

TABLE 2

| Compound | IC50 (μM) |
| --- | --- |
| CT1514 | >500 |
| CT1517 | >500 |
| CT1525 | >500 |
| CT1527 | 200 |
| CT1529 | 100 |
| CT1577 | >500 |
| CT1583 | >500 |
| CT1589 | 125 |
| CT1595 | 20 |
| CT2519 | 10 |
| CT1205 | 200 |
| CT1805 | 500 |
| CT1908 | 50 |

EXAMPLE 17

This example shows the effects of three inventive compounds on inhibition of mast cell degranulation by the serotonin release assay. This assay is described above and provides an in vitro model for an allergy and asthma therapeutic compound. Table 3 below shows the results of three inventive compounds (see Table 1 for the chemical names).

TABLE 3

| Compound | % Inhibition | Concentration (μM) |
| --- | --- | --- |
| CT1577 | 46% | 100 |
| CT1589 | 53% | 100 |
| CT1595 | 88% | 100 |
| CT1595 | 44% | 50 |

These data indicate that CT1595 may be an effective asthma therapeutic agent.

EXAMPLE 18

Figure 4:
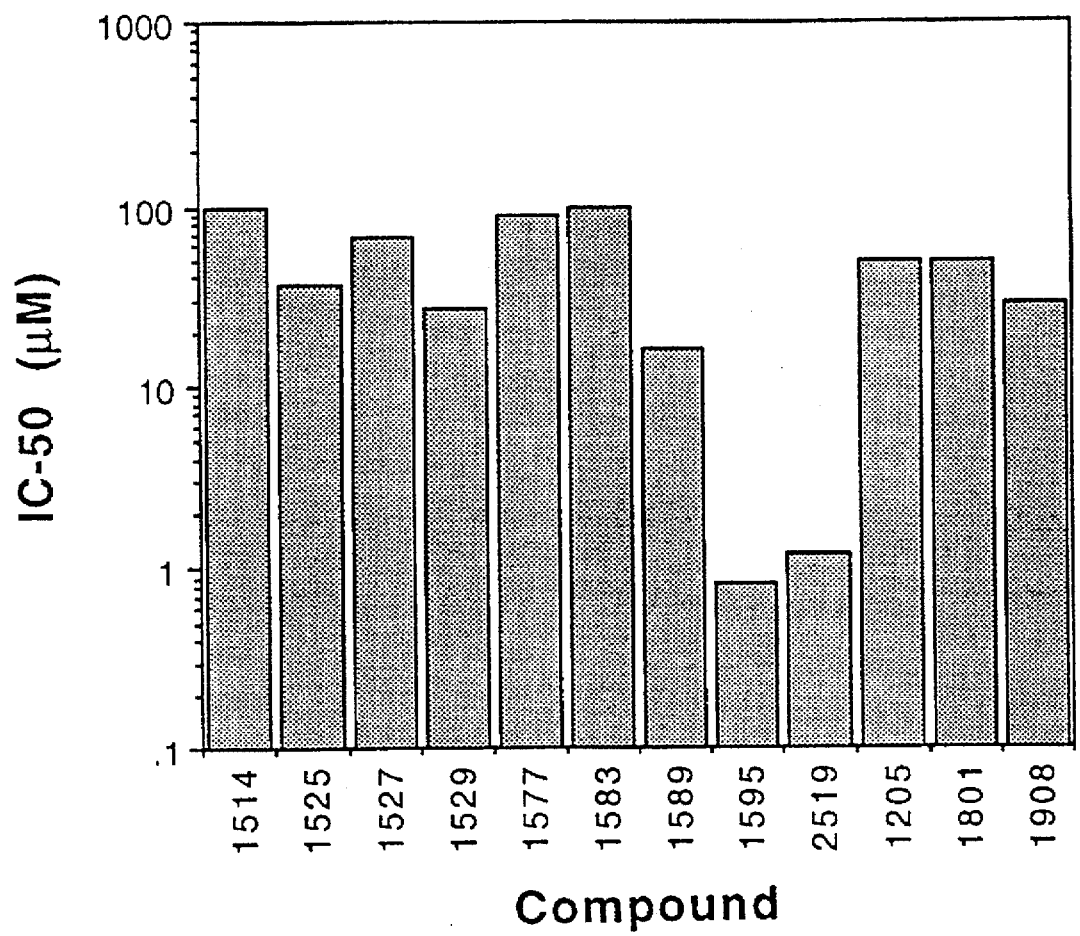
FIG. 4 shows the effects of 12 inventive compounds (see Table 1 below for chemical names) on inhibition of murine thymocyte proliferation stimulated by Concanavalin A (ConA) and interleukin-2 (IL-2). The drugs (inventive compounds) were added to the cells at the doses indicated two hours prior to activation with ConA and IL-1α. CT2519 and CT1595 were the most potent inhibitors of thymocyte proliferation in a dose-response manner. Background counts were less than 200 cpm. This in vitro assay is a model for immune suppression and treatment or prevention of autoimmune diseases.
Figure 5:
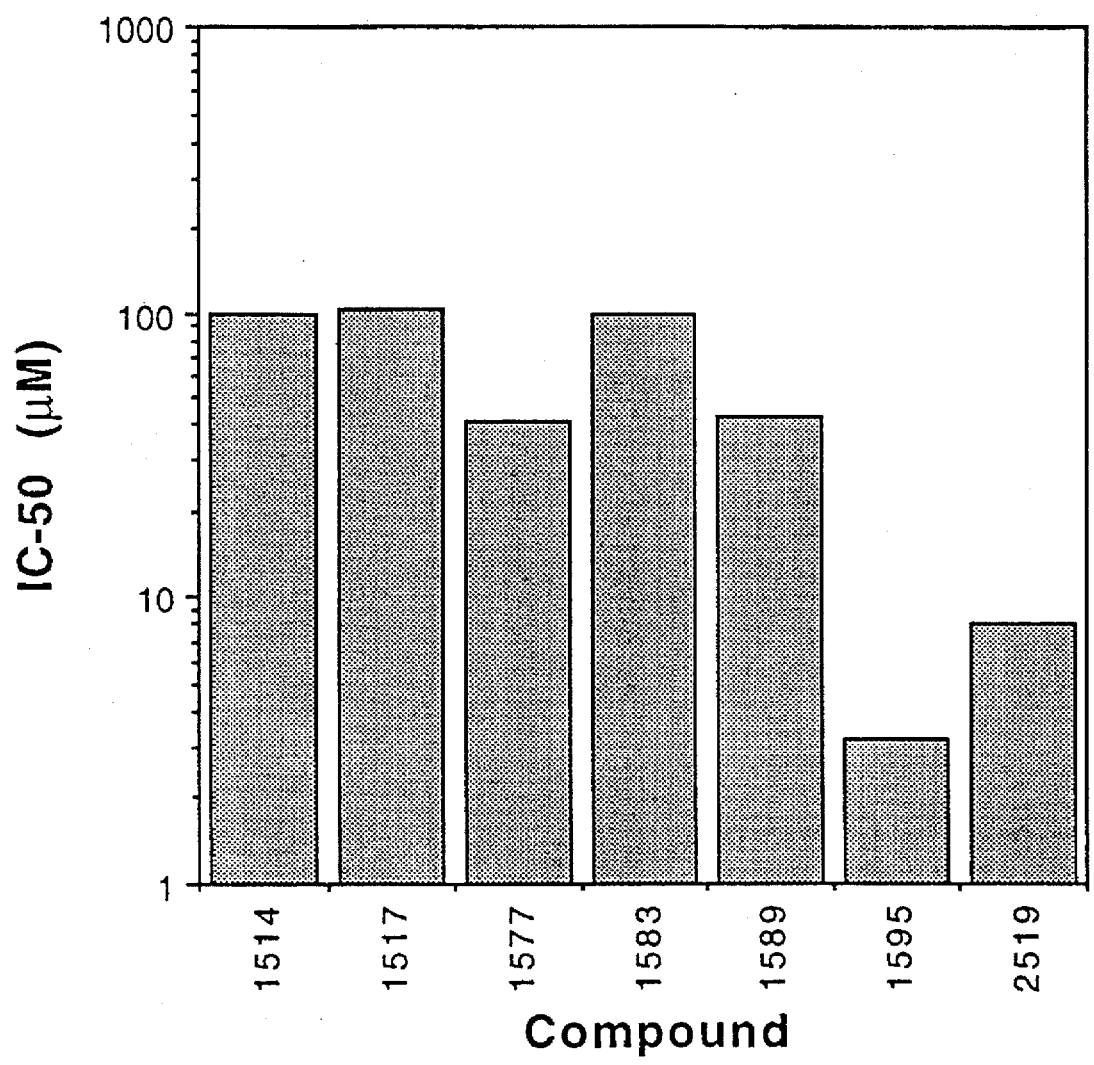
FIG. 5 shows the effects of seven inventive compounds on inhibition of murine splenocyte proliferation stimulated by anti-mu (10 μg/ml) and murine interleukin-4 (IL-4, 12.5 ng/ml). Drug was added to the cells at the doses indicated two hours prior to activation with anti-mu and IL-4. This in vitro assay is a model for immune suppression and treatment or prevention of autoimmune diseases. CT2519 and CT1595 were the most potent inhibitors of splenocyte proliferation in a dose-response manner. Background counts were less than 200 cpm.

This example illustrates the effect of CT1514, CT1525, CT1527, CT1529, CT1577, CT1583, CT1589, CT1595, CT2519, CT1205, CT1801 and CT1908 on inhibition of murine thymocyte proliferation stimulated by Concanavalin A (ConA) and interleukin-2 (IL-2) (FIG. 4). Thymuses were obtained from normal, female Balb/C mice. The thymuses were dissociated and plated into 96-well plates at a density of $2 \times 10^5$ cells/well. ConA and IL-1α were added to the wells (ConA (0.25 μg/ml) and IL-1α (12.5 ng/ml)). The cells were incubated for 4 days at 37° C. On day 4, the cells were pulsed with tritiated thymidine and allowed to incubate for an additional 4 hrs. The cells were harvested and incorporated tritiated thymidine was determined in a liquid scintillation counter. Drug was added at the doses indicated two hours prior to activation with ConA and IL-1α. CT1595 and CT2519 were the most potent drugs in this immune suppression assay. Background counts were less than 200 cpm. This in vitro assay is a model for immune suppression and treatment or prevention of autoimmune diseases.

EXAMPLE 19

This example illustrates a mixed lymphocyte reaction assay of CT1514, CT1517, CT1525, CT1527, CT1529, CT1577, CT1583, CT1595, CT2519 and CT1908. FIG. 1 shows a bar graph of IC50 values for ten inventive compounds (see Table 1 above for chemical names) in a mixed lymphocyte assay to measure immune suppression activity. The mixed lymphocyte reaction shows a proliferative response of PBMC (peripheral blood mononuclear cells) to allogeneic stimulation determined in a two-way mixed lymphocyte reaction. CT1595 and CT2519 showed dose-response activity in this immune modulating activity assay procedure with an IC50's below of 10 μM, at levels easily achievable in vivo.

Figure 2:
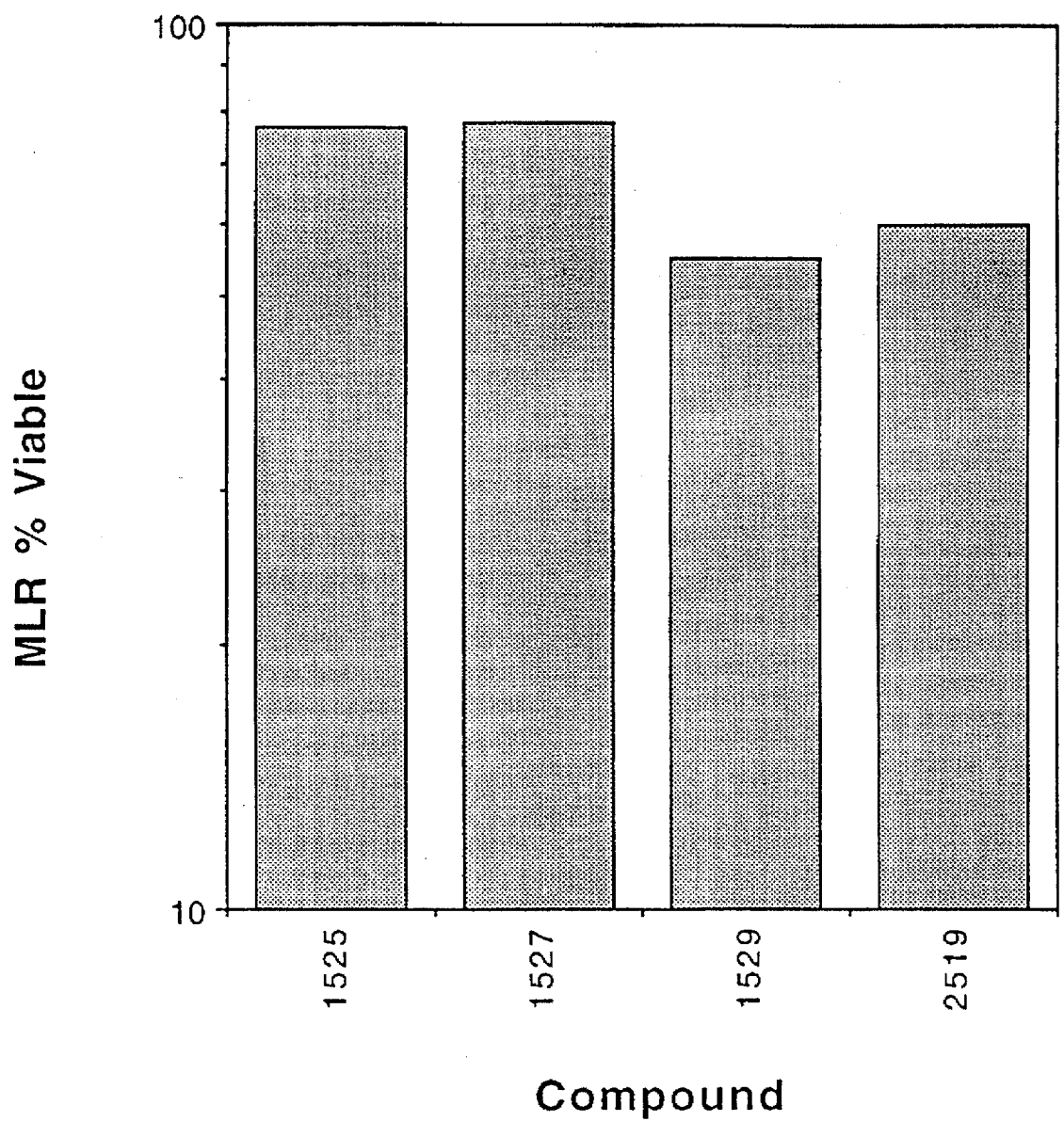
FIG. 2 shows a bar graph of the percent viable cells in mixed lymphocyte assay culture after six days of cell culture. Control cells that have not been exposed to a drug are generally 78 to 85% viable under such culture conditions. For this graph, all of the compounds were present at 100 μM, which is usually well above their IC50 concentration in this assay (see FIG. 1). One of the most potent compound, CT2519 was not cytotoxic at 100 μM but this concentration is well above its IC50 value indicating the presence of a significant therapeutic window.

FIG. 2 shows a bar graph of the percent viable cells in mixed lymphocyte assay culture after six days of cell culture. Control cells that have not been exposed to a drug are generally 78 to 85% viable under such culture conditions. For this graph, all of the compounds were present at 100 μM, which is usually well above their IC50 concentration in this assay (see FIG. 1). One of the most potent compound, CT2519 was not cytotoxic at 100 μM but this concentration is well above its IC50 value indicating the presence of a significant therapeutic window.

Figure 3:
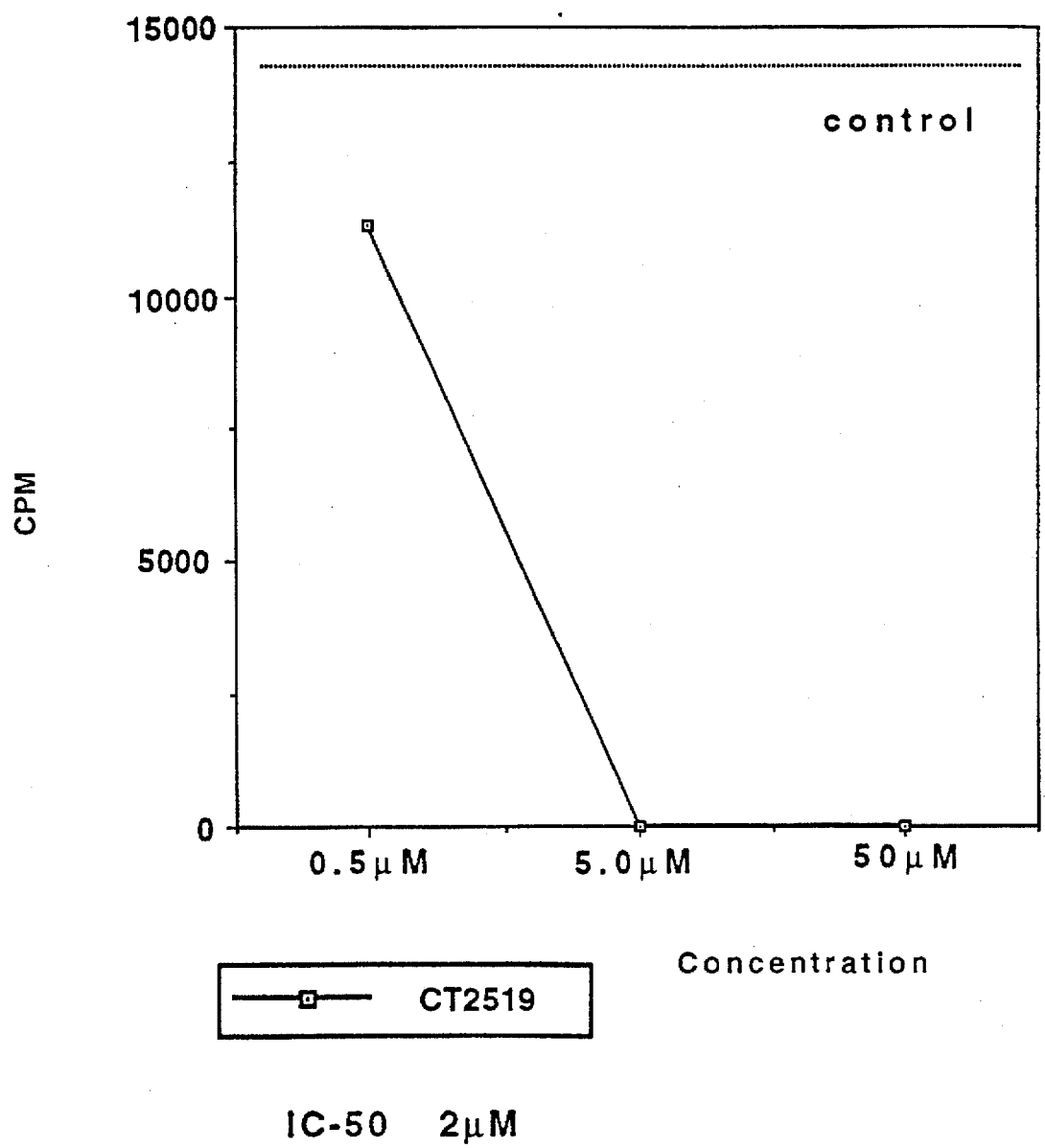
FIG. 3 shows a representative mixed lymphocyte reaction assay of CT2519 (see Table 1 below for chemical names) showing a dose response relationship for calculating IC50 values. The mixed lymphocyte reaction shows a proliferative response of PBMC to allogeneic stimulation determined in a two-way mixed lymphocyte reaction. CT2519 showed significant dose-response activity in this immune modulating activity assay procedure with an IC50 of 2 μM.

FIG. 3 shows a representative mixed lymphocyte reaction assay of CT2519 (see Table 1 above for chemical names) showing a dose response relationship for calculating IC50 values. The mixed lymphocyte reaction shows a proliferative response of PBMC to allogeneic stimulation determined in a two-way mixed lymphocyte reaction. CT2519 showed significant dose-response activity in this immune modulating activity assay procedure with an IC50 of 2 μM.

EXAMPLE 20

This example illustrates the effects of CT1514, CT1517, CT1577, CT1583, CT1589, CT1595 and CT2519 (see chemical names in Table 1 above) on inhibition of murine splenocyte proliferation stimulated by anti-mu (10 μg/ml) and interleukin-4 (IL-4, 12.5 ng/ml). This in vitro assay is described above and is an immune suppression and autoimmune treatment assay emphasizing a humoral or B cell immune response. Drug was added to the cells at the doses indicated two hours prior to activation with anti-mu and IL-4. This in vitro assay is a model for immune suppression and treatment or prevention of autoimmune diseases. CT2519 and CT1595 were the most potent inhibitors of splenocyte proliferation in a dose-response manner. Background counts were less than 200 cpm.

EXAMPLE 21

Figure 6:
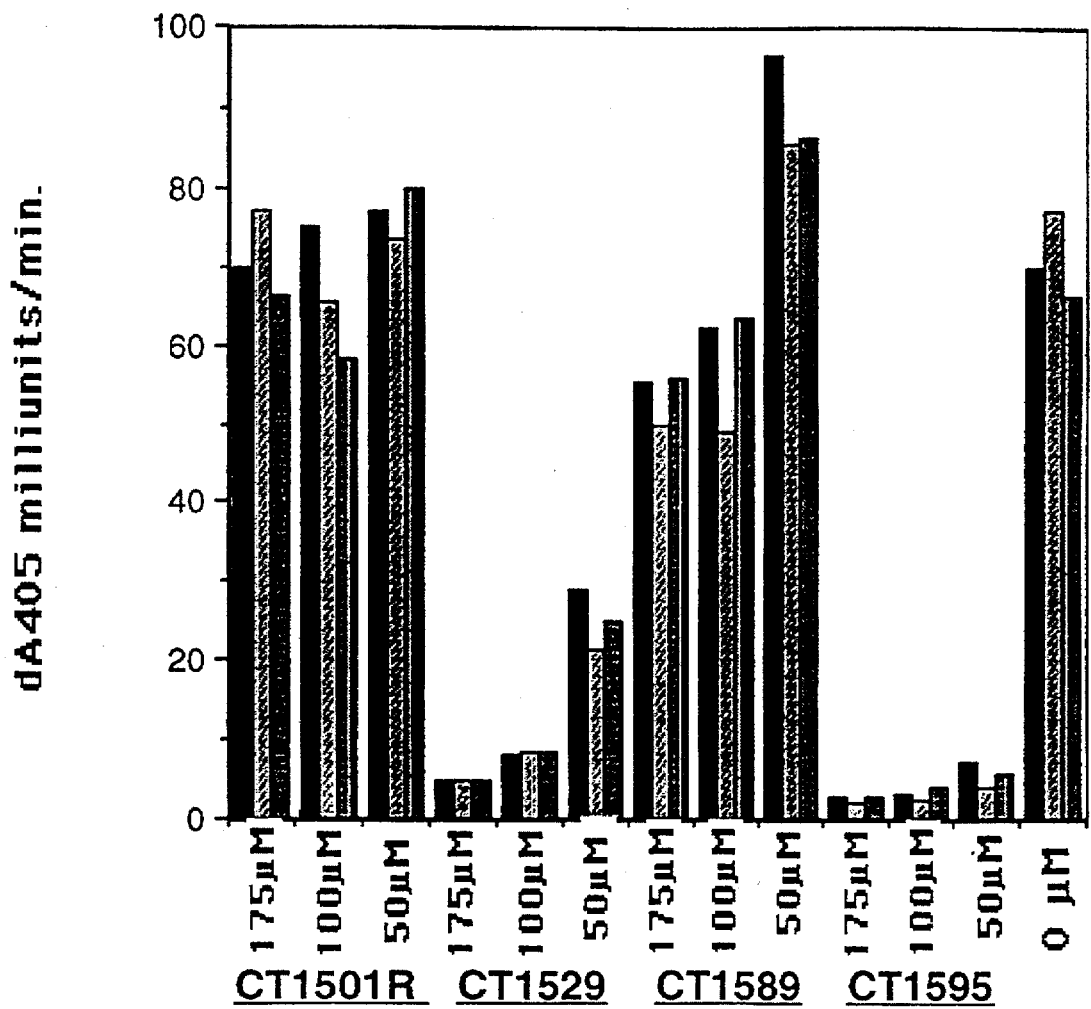
FIG. 6 shows the effects of CT1501R (a reference compound), CT1529, CT1589, and CT1595 (see Table 1 for chemical names) on yeast growth (*Saccharomyces cervisiae*) in the presence or absence of drug. This assay measures anti-yeast and anti-fungal activity of the drugs tested.

This example illustrates the effects of CT2501R (a reference compound), CT1529, CT1589 and CT1519 (see Table 1 for chemical names) on yeast growth (Saccharomyces cervisiae) in the presence or absence of drug. This assays measures anti-yeast and anti-fungal activity of the drugs tested. As shown in FIG. 6, CT1595 strongly inhibited yeast growth and is a potential topical or systemic antimicrobial drug according to this in vitro model.

EXAMPLE 22

Figure 7:
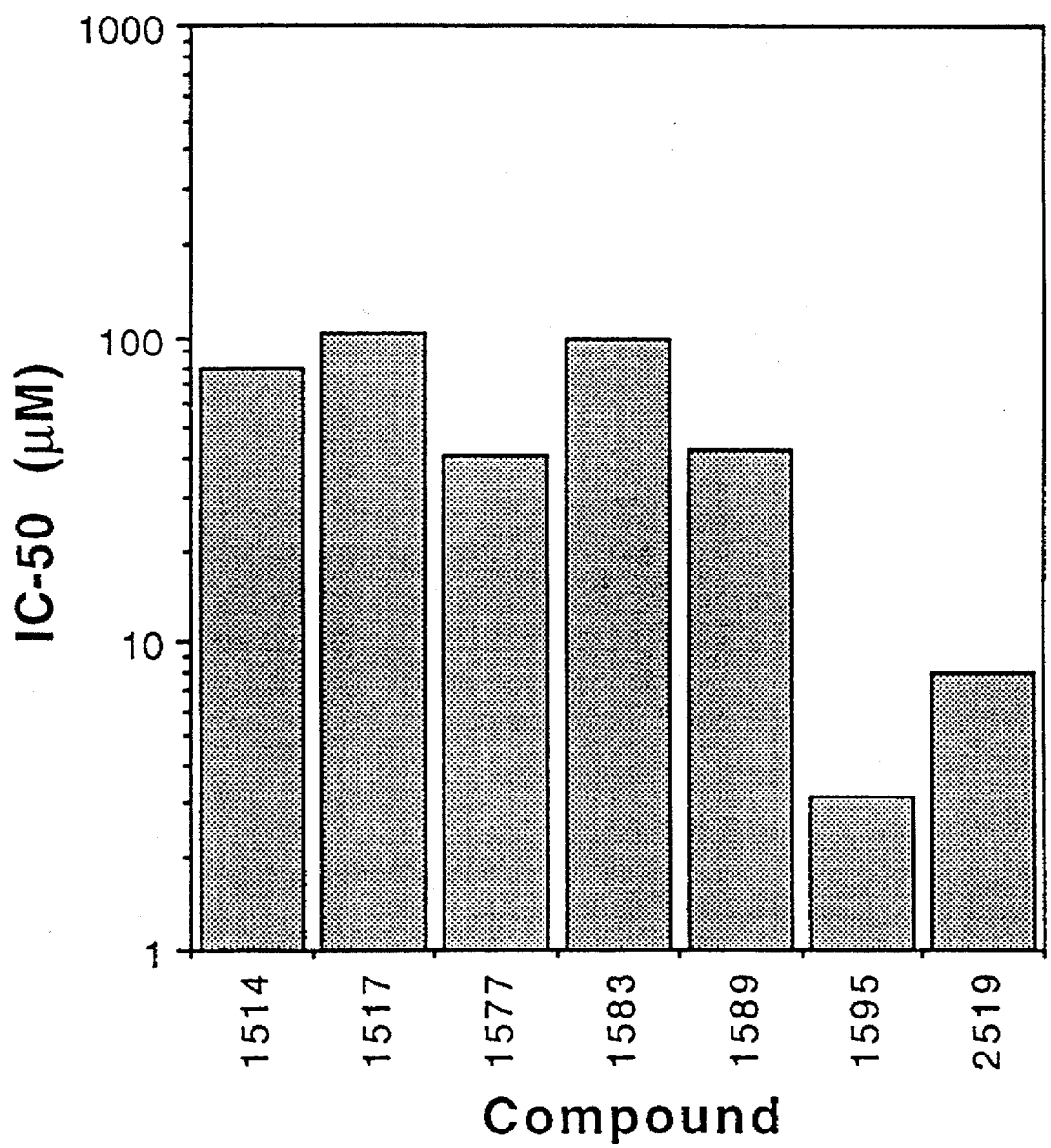
FIG. 7 illustrates the ability of seven inventive compounds (see Table 1 for chemical names) to strongly inhibit proliferation of human stromal cells when stimulated with PDGF and IL-1. This assay is a model for restenosis and treatment of atherosclerosis and coronary artery disease. Stromal cells were starved in serum-free media for one day and then stimulated with 50 ng/ml PDGF-BB. The drags were added at the indicated concentrations one hour prior to PDGF stimulation. Tritiated thymidine was added for one day at the time of PDGF stimulation and the cells were harvested and counted by liquid scintillation counting 24 hrs later. Background counts (i.e., starved cells) were approximately 1% of control levels.

This example illustrates the effects of CT1514, CT1517, CT1577, CT1583, CT1589, CT1595 and CT2519 (see Table 1 above for chemical structures) to strongly inhibit proliferation of human stromal cells when stimulated with PDGF. This assay is a model for restenosis and treatment of atherosclerosis and coronary artery disease. Stromal cells were starved in serum-free media for one day and then stimulated with 50 ng/ml PDGF-BB. The drugs were added at the indicated concentrations one hour prior to PDGF stimulation. Tritiated thymidine was added for one day at the time of PDGF stimulation and the cells were harvested and counted by liquid scintillation counting 24 hrs later. Background counts (i.e., starved cells) were approximately 1% of control levels. FIG. 7 shows that all drugs were active in this predictive in vitro model with CT1595 and CT2519 showing the most potent activity.

EXAMPLE 23

Figure 8:
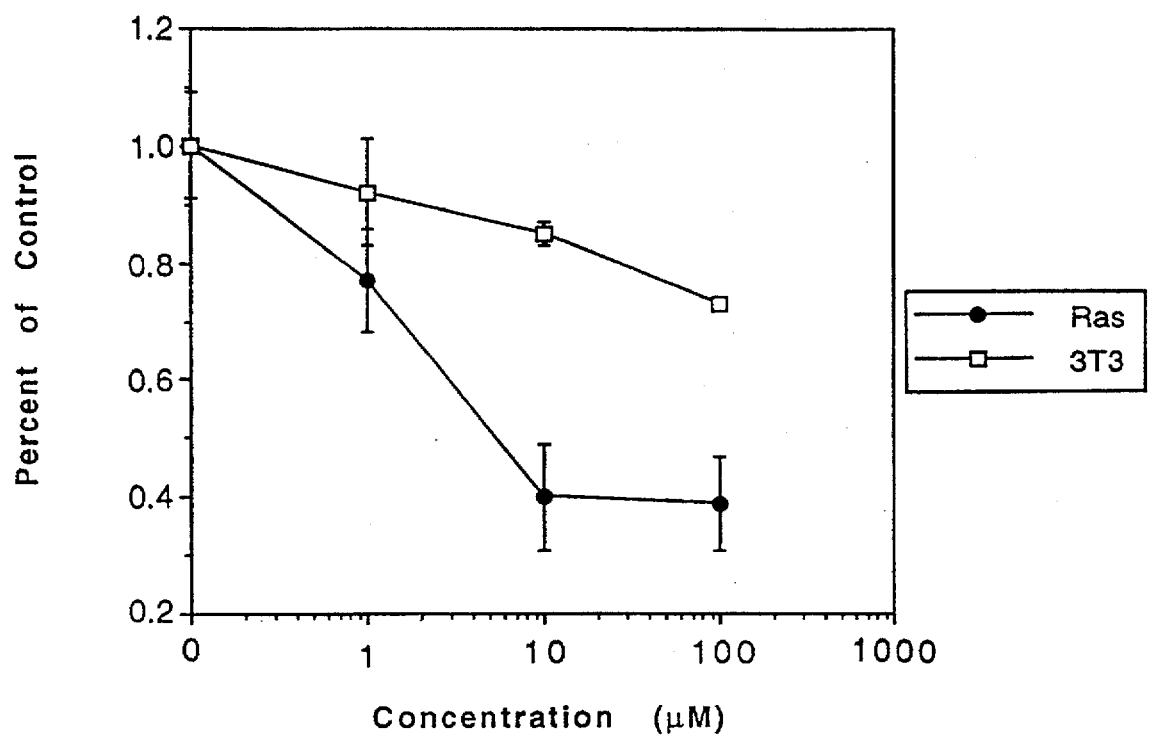
FIG. 8 shows a comparison of cytotoxicity determinations for CT1595 in transformed cells (Ras 3T3) and in normal 3T3 cells at drug doses of 1, 10 and 100 μM. At each concentration tested, CT1595 was more cytotoxic for the cancer cell than the normal cell indicating differential toxicity for tumor cells and potential usefulness as a cancer chemotherapeutic agent. A similar experiment is shown in FIG. 9 for five inventive compounds (see Table 1 below for chemical names) showing differential cytotoxicity for the same normal and transformed cells. Only CT1529 and CT1595 showed significant cytotoxic activity in this in vitro model for cancer chemotherapeutic agent applications.
Figure 9:
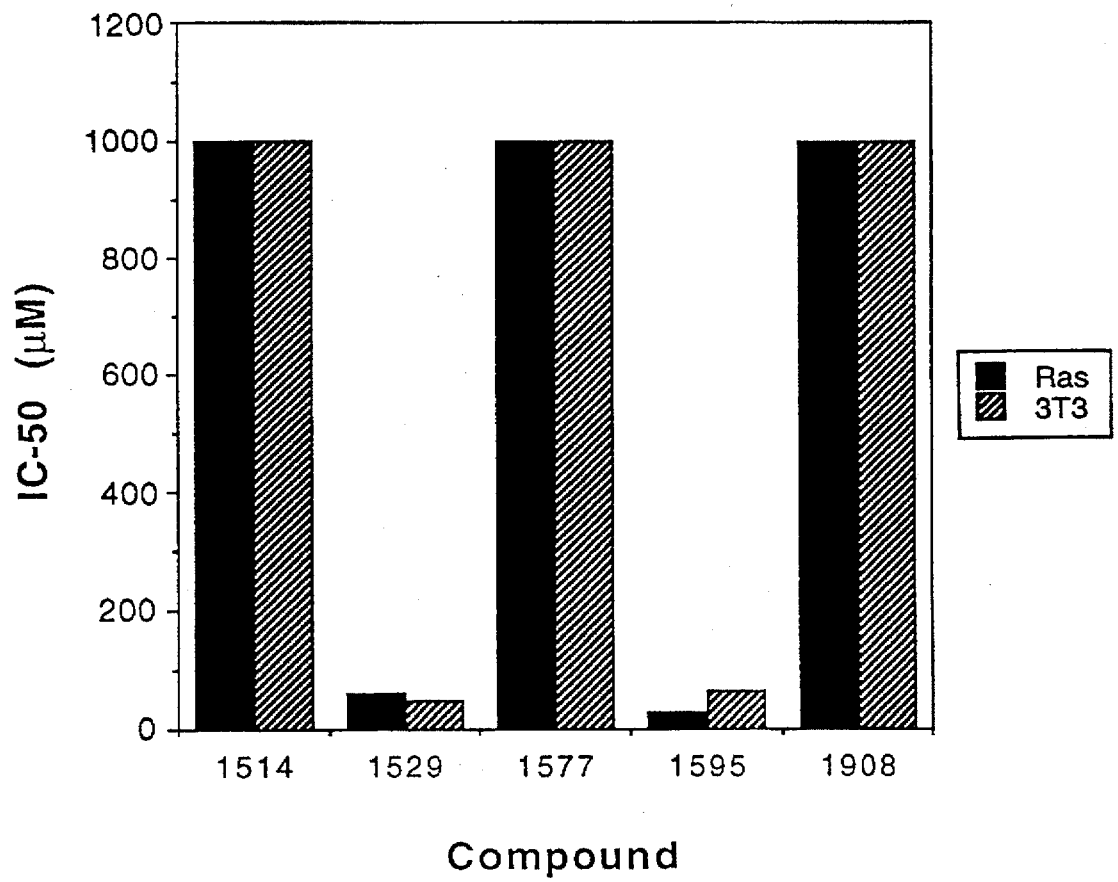

This example illustrates a comparison of cytotoxicity determinations for CT1595 in transformed cells (Ras 3T3) and in normal 3T3 cells at drug doses of 1, 10 and 100 µM in in vitro cell culture conditions (FIG. 8). At each concentration tested, CT1595 was more cytotoxic for the cancer cell than the normal cell indicating differential toxicity for tumor cells and potential usefulness as a cancer chemotherapeutic agent. A similar experiment is shown in FIG. 9 for five inventive compounds (see Table 1 above for chemical names) showing differential cytotoxicity for the same normal and transformed cells. Only CT1529 and CT1595 showed significant cytotoxic activity in this in vitro model for cancer chemotherapeutic agent applications.

EXAMPLE 24

Figure 10:
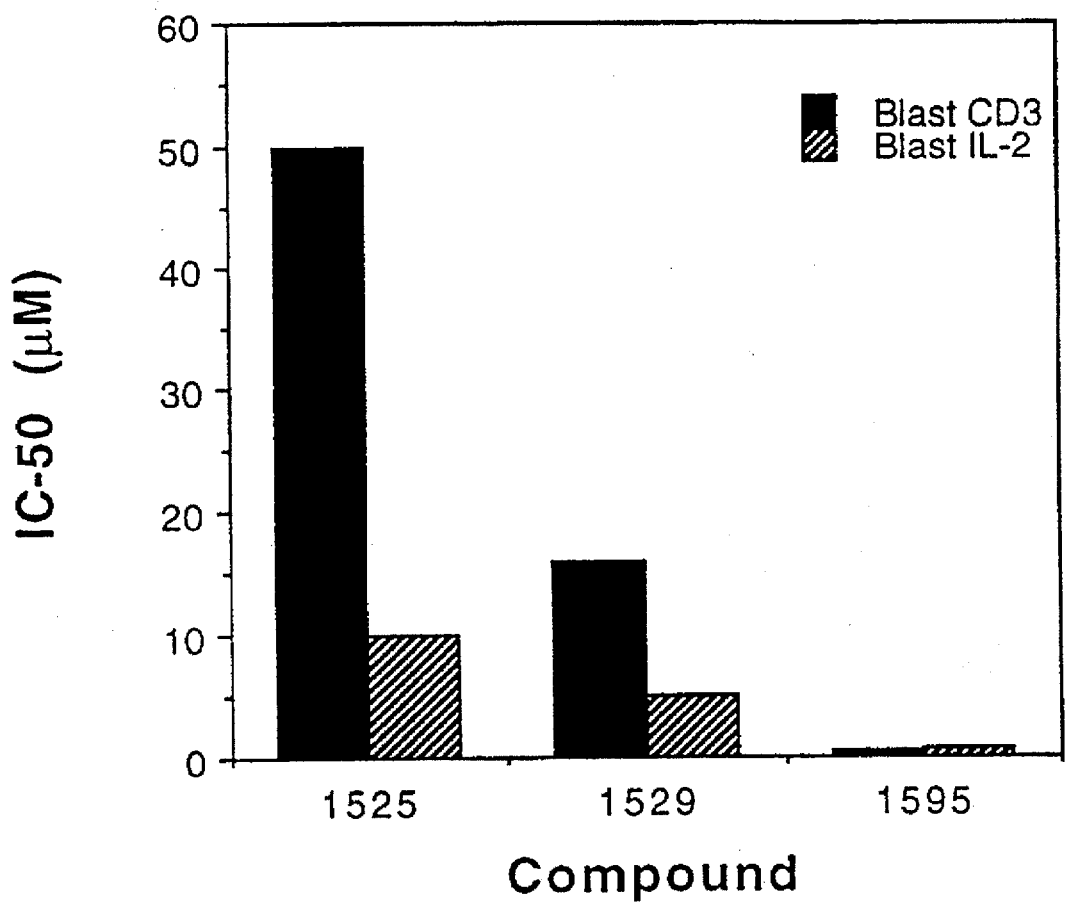
FIG. 10 shows the effects of three inventive compounds on inhibition of blast formation from human lymphocytes stimulated by IL-2 or an anti-CD3 antibody. This is a human in vitro assay for immunosuppressive activity of the inventive compounds. Of the three compounds tested, CT1595 demonstrated significant immunosuppressive activity of blastogenesis stimulated by either IL-2 or anti-CD3 with IC50 values below 5 μM.

This example illustrates an experiment showing the effects of CT1525, CT1529 and CT1595 (see Table 1 above for chemical names) on inhibition of blast formation from human lymphocytes stimulated by IL-2 or an anti-CD3 antibody (FIG. 10). This is a human in vitro assay for immunosuppressive activity of the inventive compounds. Of the three compounds tested, CT1595 demonstrated significant immunosuppressive activity of blastogenesis stimulated by either IL-2 or anti-CD3 with IC50 values below 5 µM.

EXAMPLE 25

Figure 11:
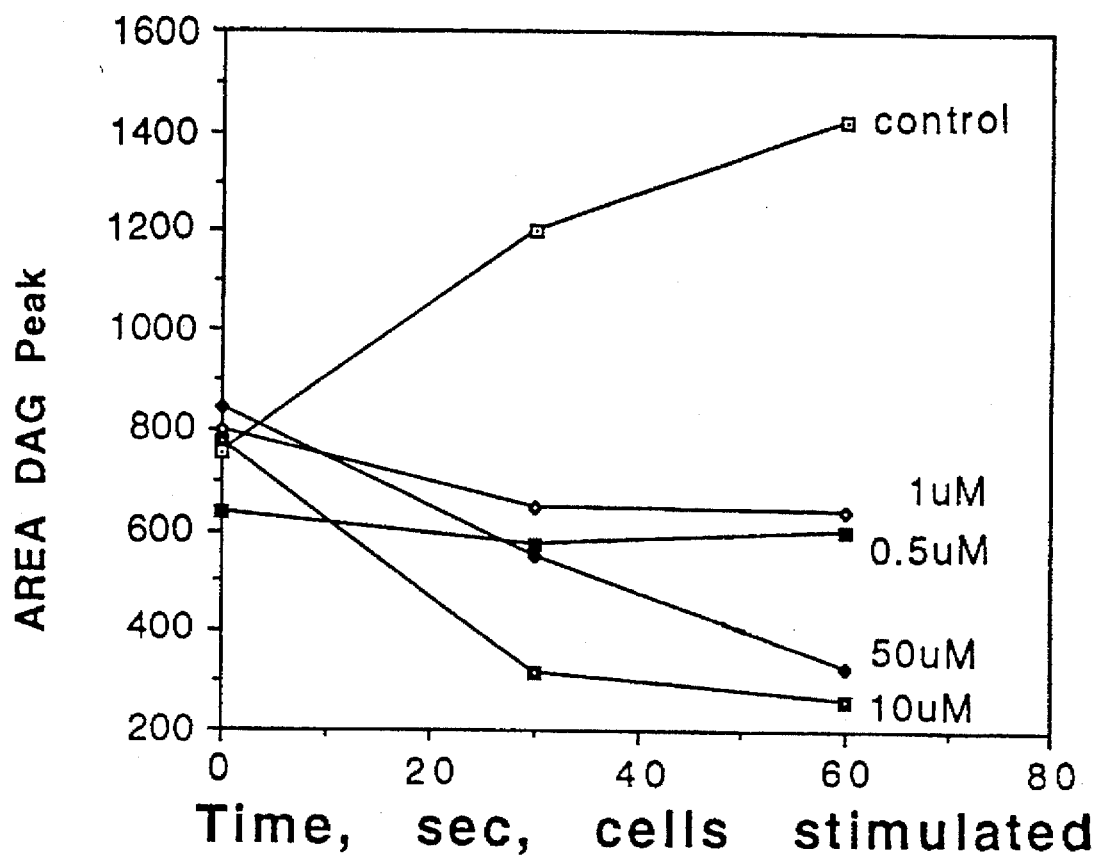
FIGS. 11 and 12 show the effects of CT1595 on the amount of DAG (diacylglycerol) (FIG. 11) and PA (Phosphatidic acid) (FIG. 12) generated at different times after stimulation of Ras-transformed 3T3 cells with IL-1β. CT1595 is a potent drug to inhibit enzyme activity that generates PA and then DAG by inhibiting IL-1-induced signal transduction, through this second messenger pathway, via the Type I IL-1 receptor. The inhibiting activity was not in a dose-response manner, indication that the IC50 concentration for inhibiting cellular second messenger signaling is probably below 500 nM. It is not evident which enzyme or enzymes are being inhibited by CT1595, however, the overall signal is being significantly inhibited and this is corroborated by the effects of this compounds in vitro on other predictive models of disease.
Figure 12:
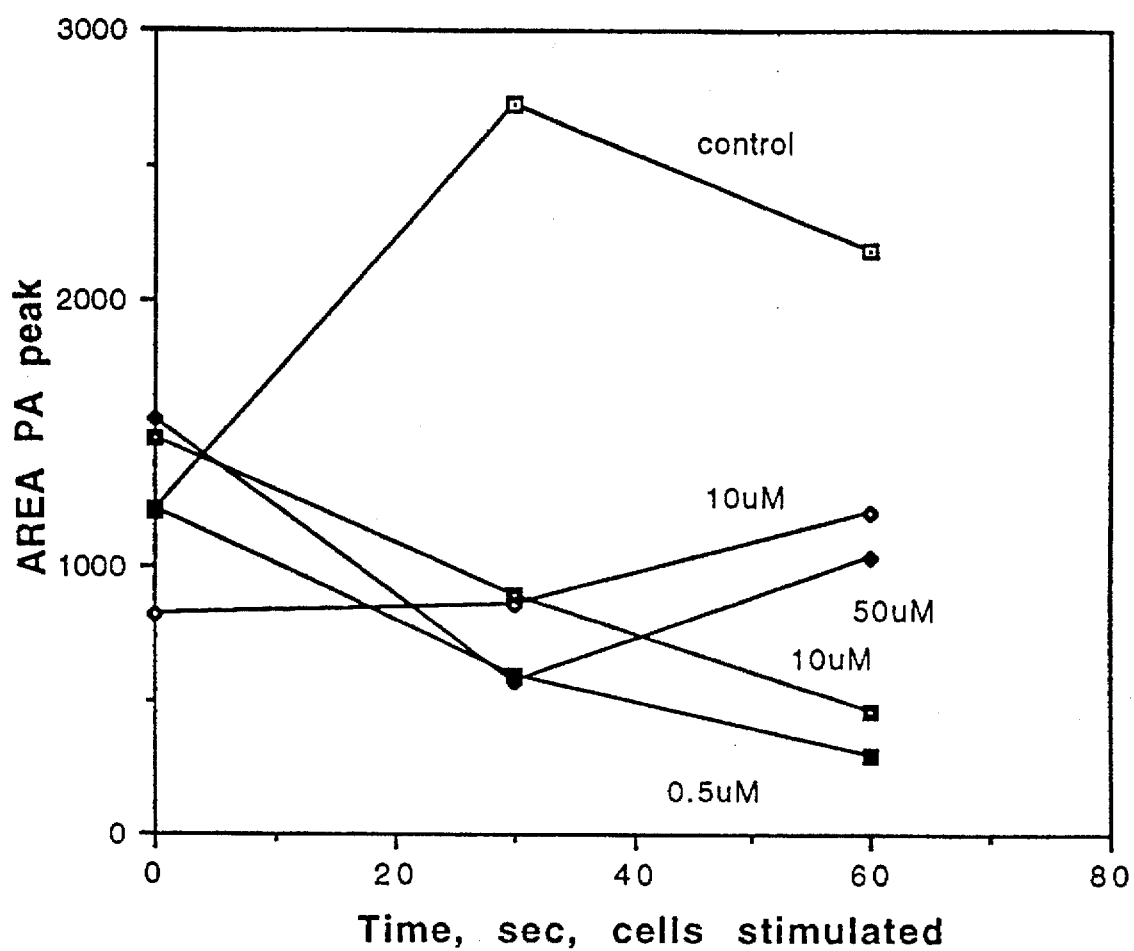

This example illustrates the effects of CT1595 on the amount of DAG (diacylglycerol) (FIG. 11) and PA (Phosphatidic acid) (FIG. 12) generated at different times after stimulation of Ras-transformed 3T3 cells with IL-1β. CT1595 is a potent drug to inhibit enzyme activity that generates PA and then DAG by inhibiting IL-1-induced signal transduction, through this second messenger pathway, via the Type I IL-1 receptor. The inhibiting activity was not in a dose-response manner, indicating that the IC50 concentration for inhibiting cellular second messenger signaling is probably below 500 nM. It is not evident which enzyme or enzymes are being inhibited by CT1595. However, the overall signal is being significantly inhibited and this is corroborated by the effects of this compounds in vitro on other predictive models of disease.

Figure 13:
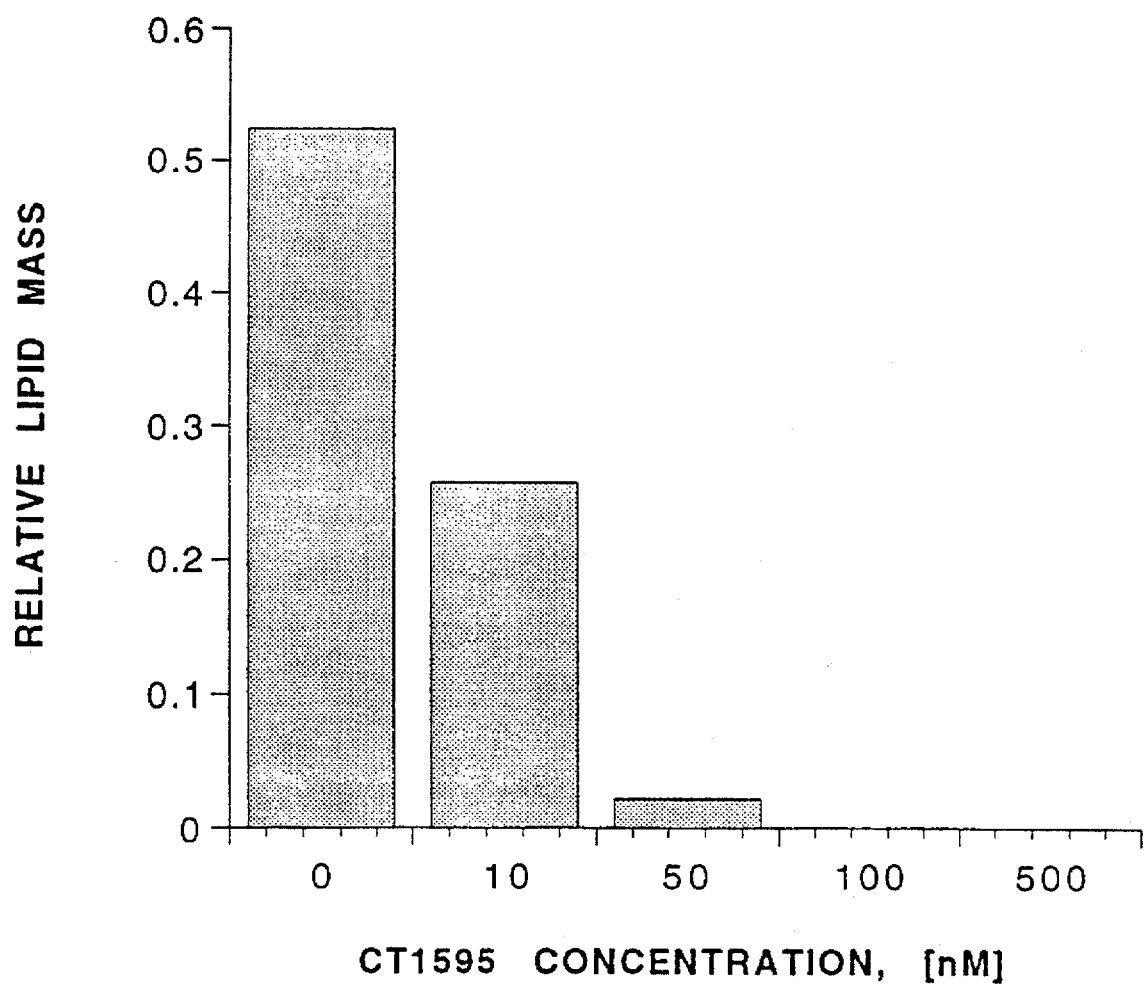
FIG. 13 shows the effect of different nanomolar concentrations of CT1595 on the total PA mass in a mast cell line (PT-18) stimulated by administration of IgE and dinitrophenol (DNP). These data show that the IC50 of CT1595 is in the low nanomolar range for accumulation of PA.

FIG. 13 shows the effect of different nanomolar concentrations of CT1595 on the total PA mass in a mast cell line (PT-18) stimulated by administration of IgE and dinitrophenol (DNP). These data show that the IC50 of CT1595 is in the low nanomolar range for accumulation of PA.

EXAMPLE 26

Figure 14:
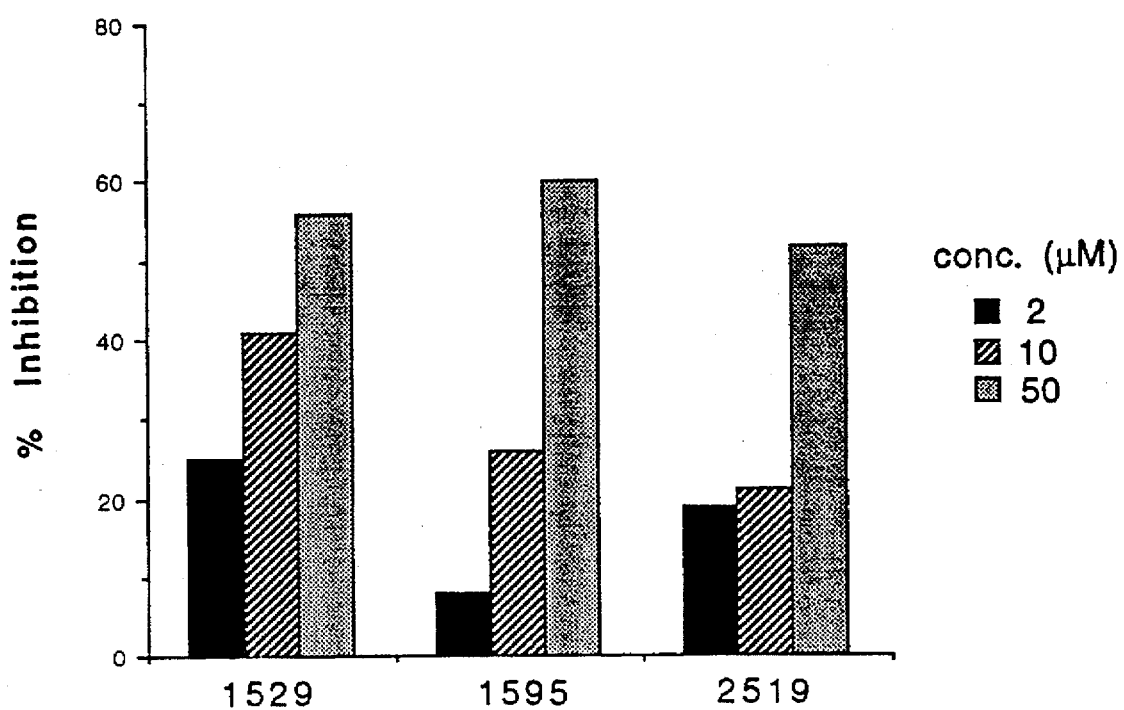
FIG. 14 shows a comparison of CT1595, CT1529 and CT2519 in an ex vivo human TNF model which is a predictive model for treatment and prevention of septic shock and sepsis syndrome. This model adds LPS to whole blood (normal human volunteers) to trigger a dose-dependent synthesis and extracellular release of TNF according to Desch et al. (*Lymphokine Res.* 8:141, 1989). The ex vivo model examines whether LPS-mediated release of TNF from monocytes in whole blood can be block by an inventive compound. All three inventive compounds tested could block TNF release in a dose-dependent fashion. However, CT1529 was the most effective agent at lower doses.

This example illustrates a comparative experiment comparing CT1595, CT1529 and CT2519 in an ex vivo human TNF model described herein. This assay is a predictive model for treatment and prevention of septic shock and sepsis syndrome. This model adds LPS to whole blood (normal human volunteers) to trigger a dose-dependent synthesis and extracellular release of TNF according to Desch et al. (*Lymphokine Res.* 8:141, 1989). The ex vivo model examines whether LPS-mediated release of TNF from monocytes in whole blood can be block by an inventive compound. All three inventive compounds tested could block TNF release in a dose-dependent fashion (FIG. 14).

However, CT1529 was the most effective agent at lower doses that are likely achievable in vivo.

We claim:

1. A compound having the formula:

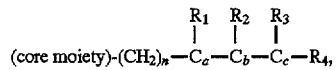

(core moiety)-(CH$_2$)$_n$—C$_a$—C$_b$—C$_c$—R$_4$, wherein n is an integer from 5 to 9, wherein the core moiety is a xanthine, wherein C$_a$, C$_b$, and C$_c$ are an R or S enantiomer or racemic mixture and the C$_a$, C$_b$, and C$_c$ carbon atoms are bonded together by a single bond, double bond, or ether linkage, wherein R$_1$, R$_2$ and R$_3$ are independently halo, hydroxy, hydrogen, keto, isothiocyano, azide or haloacetoxy with the proviso that at least one of R$_1$, R$_2$ or R$_3$ must be a halo, isothiocyano, azide or haloacetoxy group, wherein R$_4$ is hydrogen, C$_{1-6}$ alkyl, C$_{1-6}$ alkenyl, cyclo C$_{4-6}$ alkyl, or phenyl, and wherein halo refers to fluoro, chloro, bromo and iodo.

2. The compound of claim 1 wherein, R$_2$ is hydrogen, R$_1$ and R$_3$ are independently a halo and a keto or a hydroxy group, and n is an integer from 5–6.

3. The compound of claim 2 wherein the halo group is a chloro or fluoro group.

4. The compound of claim 1 wherein the core moiety is selected from the group consisting of xanthine, halogen-substituted xanthines, 3,7-dimethylxanthine, 3-methylxanthine, 3-methyl-7-methylpivaloylxanthine, 8-amino-3-methylxanthine, 7-methylhypoxanthine.

5. The compound of claim 1 comprising 1-(5-isothiocyanatohexyl)3,7-dimethylxanthine.

6. The compound of claim 1 comprising 1-(6-chloro-5-oxohexyl)3,7-dimethylxanthine.

7. The compound of claim 1 comprising 1-(6-azidohexyl) 3,7-dimethylxanthine.

8. The compound of claim 1 comprising 1-(9-acetoxy-10-bromodecyl(3,7-dimethylxanthine.

9. The compound of claim 1 comprising 1-(6-bromohexyl)3,7-dimethylxanthine (CT1589).

10. The compound of claim 1 comprising 1-(5-fluorohexyl)3,7-dimethylxanthine.

11. The compound of claim 1 comprising 1-[5-(chloroacetoxy)hexyl]3,7-dimethylxanthine.

12. The compound of claim 1 comprising 1-[6-(chloroacetoxy)hexyl]3,7-dimethylxanthine.

13. The compound of claim 1 comprising 1-(6-chlorohexyl)3,7-dimethylxanthine.

14. The compound of claim 1 comprising 1-(6-azido-5-hydroxyhexyl)3,7-dimethylxanthine.

15. The compound of claim 1 comprising 1-(7-acetoxy-8-bromooctyl)3,7-dimethylxanthine.

16. A pharmaceutical composition comprising a compound of claim 1 and a pharmaceutically acceptable excipient, wherein the pharmaceutical composition is formulated for oral, parenteral, ex vivo or topical administration to a patient.

17. The pharmaceutical composition of claim 16 wherein the oral dose of compound is from about 500 mg to about 1500 mg twice or three times daily, the parenteral dose is from about 1.0 g to about 5.0 g administered (i.v., i.p., i.m., or s.c.) over a course of 24 hours, the topical formulation concentration is from about 1% to about 4% by weight, and the ex vivo culture concentration is from about 10 nM to about 500 µM.

* * * * *